(12) United States Patent
Boschee et al.

(10) Patent No.: US 12,706,193 B2
(45) Date of Patent: Aug. 11, 2026

(54) LOCAL ACCESS TO SITUATION REPORTS USING A WEARABLE MEDICAL DEVICE

(71) Applicant: West Affum Holdings Designated Activity Company, Dublin (IE)

(72) Inventors: Jeffrey M. Boschee, Woodinville, WA (US); Brian D. Webster, Mercer Island, WA (US)

(73) Assignee: West Affum Holdings DAC, Dublin (IE)

( * ) Notice: Subject to any disclaimer, the term of this patent is extended or adjusted under 35 U.S.C. 154(b) by 252 days.

(21) Appl. No.: 18/443,042

(22) Filed: Feb. 15, 2024

(65) Prior Publication Data

US 2024/0282420 A1 Aug. 22, 2024

Related U.S. Application Data

(63) Continuation-in-part of application No. 18/544,397, filed on Dec. 18, 2023.

(Continued)

(51) Int. Cl.
*G16H 15/00* (2018.01)
*A61B 5/00* (2006.01)

(Continued)

(52) U.S. Cl.
CPC ........... *G16H 15/00* (2018.01); *A61B 5/0006* (2013.01); *A61B 5/002* (2013.01); *A61B 5/1112* (2013.01);

(Continued)

(58) Field of Classification Search
CPC ........ G16H 15/00; G16H 10/60; G16H 40/67; A61B 5/0006; A61B 5/002; A61B 5/1112;

(Continued)

(56) References Cited

U.S. PATENT DOCUMENTS 3,724,355 A 4/1973 Busch et al.
3,724,455 A 4/1973 Unger (Continued)

FOREIGN PATENT DOCUMENTS

DE 102005060985 A2 6/2007
EP 2305110 A1 4/2011

(Continued)

OTHER PUBLICATIONS

Heartstart MRx and XL AED Algorithm—Application Note, Jul. 2001, Edition 2 Philips Healthcare, USA.

(Continued)

*Primary Examiner* — Ryan W Sherwin
(74) *Attorney, Agent, or Firm* — Lisa Benado, Propel IP Law, PLLC

(57) ABSTRACT

Access to a situation report about a patient experiencing a medical event is provided via a short range connection, such as a BLE connection, between a wearable medical device and a communication device of a trained support person. The wearable medical device is worn by the patient and gathers patient data related to the medical event, such as an arrythmia. Patient data are processed into situation information which is formatted for easy translation by the communication device into the situation report. The resulting situation report is accessible by the trained support person via the communication device with relevant information to assist in providing medical support for the patient.

20 Claims, 9 Drawing Sheets

Related U.S. Application Data

(60) Provisional application No. 63/446,486, filed on Feb. 17, 2023.

(51) Int. Cl.

| | |
|---|---|
| ***A61B 5/11*** | (2006.01) |
| ***A61B 5/33*** | (2021.01) |
| ***A61B 5/332*** | (2021.01) |
| ***A61B 5/339*** | (2021.01) |
| ***A61B 5/364*** | (2021.01) |
| ***A61N 1/39*** | (2006.01) |
| ***G16H 10/60*** | (2018.01) |
| ***G16H 40/67*** | (2018.01) |

(52) U.S. Cl.
CPC ................ *A61B 5/33* (2021.01); *A61B 5/332* (2021.01); *A61B 5/339* (2021.01); *A61B 5/364* (2021.01); *A61N 1/3904* (2017.08); *A61N 1/3993* (2013.01); *G16H 10/60* (2018.01); *G16H 40/67* (2018.01)

(58) Field of Classification Search
CPC ........... A61B 5/33; A61B 5/332; A61B 5/339; A61B 5/364; A61N 1/3904; A61N 1/3993; A61N 1/046; A61N 1/3925
See application file for complete search history.

(56) References Cited

U.S. PATENT DOCUMENTS 4,583,524 A 4/1986 Hutchins
4,619,265 A 10/1986 Morgan et al.
4,666,432 A 5/1987 McNeish et al.
4,698,848 A 10/1987 Buckley
4,928,690 A 5/1990 Heilman et al.
4,955,381 A 9/1990 Way et al.
5,078,134 A 1/1992 Heilman et al.
5,228,449 A 7/1993 Christ et al.
5,348,008 A 9/1994 Bornn et al.
5,353,793 A 10/1994 Bornn
RE34,800 E 11/1994 Hutchins
5,394,892 A 3/1995 Kenny et al.
5,405,362 A 4/1995 Kramer et al.
5,429,593 A 7/1995 Matory
5,474,574 A 12/1995 Payne et al.
5,618,208 A 4/1997 Crouse et al.
5,662,690 A 9/1997 Cole et al.
5,708,978 A 1/1998 Johnsrud
5,741,306 A 4/1998 Glegyak et al.
5,782,878 A 7/1998 Morgan et al.
5,792,204 A 8/1998 Snell
5,902,249 A 5/1999 Lyster
5,913,685 A 6/1999 Hutchins
5,944,669 A 8/1999 Kaib
6,047,203 A 4/2000 Sackner et al.
6,065,154 A 5/2000 Hulings et al.
6,108,197 A 8/2000 Janik
6,148,233 A 11/2000 Owen et al.
6,201,992 B1 3/2001 Freeman
6,263,238 B1 7/2001 Brewer et al.
6,280,461 B1 8/2001 Glegyak et al.
6,287,328 B1 9/2001 Snyder et al.
6,304,780 B1 10/2001 Owen et al.
6,319,011 B1 11/2001 Motti et al.
6,334,070 B1 12/2001 Nova et al.
6,356,785 B1 3/2002 Snyder et al.
6,427,083 B1 7/2002 Owen et al.
6,437,083 B1 8/2002 Brack et al.
6,450,942 B1 9/2002 Lapanashvili et al.
6,529,875 B1 3/2003 Nakajima et al.
6,546,285 B1 4/2003 Owen et al.
6,671,545 B2 12/2003 Fincke
6,681,003 B2 1/2004 Linder et al.
6,762,917 B1 7/2004 Verbiest et al.
7,065,401 B2 6/2006 Worden
7,099,715 B2 8/2006 Korzinov
7,212,850 B2 5/2007 Prystowsky
7,559,902 B2 7/2009 Ting et al.
7,587,237 B2 9/2009 Korzinov
7,753,759 B2 7/2010 Pintor et al.
7,865,238 B2 1/2011 Brink
7,870,761 B2 1/2011 Valentine et al.
7,907,996 B2 3/2011 Prystowsky
7,941,207 B2 5/2011 Korzinov
7,974,689 B2 7/2011 Volpe et al.
8,135,462 B2 3/2012 Owen et al.
8,140,154 B2 3/2012 Donnelly et al.
8,369,944 B2 2/2013 Macho et al.
8,527,028 B2 9/2013 Kurzweil et al.
8,548,557 B2 10/2013 Garstka et al.
8,560,044 B2 10/2013 Kurzweil et al.
8,615,295 B2 12/2013 Savage et al.
8,644,925 B2 2/2014 Volpe et al.
8,676,313 B2 3/2014 Volpe et al.
8,706,255 B2 4/2014 Phillips et al.
8,742,349 B2 6/2014 Urbon et al.
8,897,860 B2 11/2014 Volpe et al.
8,904,214 B2 12/2014 Volpe et al.
8,965,500 B2 2/2015 Macho et al.
9,008,801 B2 4/2015 Kaib et al.
9,084,583 B2 7/2015 Mazar et al.
9,089,685 B2 7/2015 Sullivan et al.
9,119,547 B2 9/2015 Cazares et al.
9,131,901 B2 9/2015 Volpe et al.
9,132,267 B2 9/2015 Kaib
9,265,432 B2 2/2016 Warren et al.
9,345,898 B2 5/2016 Piha et al.
9,408,548 B2 8/2016 Volpe et al.
9,445,719 B2 9/2016 Libbus et al.
9,454,219 B2 9/2016 Volpe et al.
9,579,020 B2 2/2017 Libbus et al.
9,592,403 B2 3/2017 Sullivan
9,598,799 B2 3/2017 Shoshani et al.
9,659,484 B1 5/2017 Mehta et al.
9,675,804 B2 6/2017 Whiting et al.
9,724,008 B2 8/2017 Sullivan et al.
9,878,171 B2 1/2018 Kaib
9,895,105 B2 2/2018 Romem
9,901,741 B2 2/2018 Chapman et al.
RE46,926 E 7/2018 Bly et al.
10,076,656 B2 9/2018 Dar et al.
10,192,387 B2 1/2019 Brinig et al.
10,307,133 B2 6/2019 Kaib
10,447,865 B2 10/2019 Mehta et al.
10,463,867 B2 11/2019 Kaib et al.
10,589,110 B2 3/2020 Oskin et al.
10,599,814 B2 3/2020 Landrum et al.
11,210,919 B2 12/2021 Beyer et al.
11,641,575 B2 5/2023 Horelik et al.
11,659,375 B2 5/2023 Anand et al.
11,741,819 B2 8/2023 Katz et al.
11,818,639 B2 11/2023 Horelik et al.
12,020,548 B2 6/2024 Jafri et al.
12,047,858 B2 7/2024 Anand
12,063,581 B2 8/2024 Martin et al.
2002/0181680 A1 12/2002 Linder et al.
2003/0004547 A1* 1/2003 Owen .................... A61N 1/046 607/5
2003/0158593 A1 8/2003 Heilman et al.
2005/0107833 A1 5/2005 Freeman et al.
2005/0107834 A1 5/2005 Freeman et al.
2006/0173499 A1 8/2006 Hampton et al.
2008/0312709 A1 12/2008 Volpe et al.
2009/0005827 A1 1/2009 Weintraub et al.
2010/0007413 A1 1/2010 Herleikson et al.
2010/0298899 A1 11/2010 Donnelly et al.
2011/0022105 A9 1/2011 Owen et al.
2011/0288604 A1 11/2011 Kaib et al.
2011/0288605 A1 11/2011 Kaib et al.
2012/0112903 A1 5/2012 Kaib et al.
2012/0144551 A1 6/2012 Guldalian
2012/0150008 A1 6/2012 Kaib et al.
2012/0158075 A1 6/2012 Kaib et al.

(56) References Cited

U.S. PATENT DOCUMENTS

| | | | |
|---|---|---|---|
| 2012/0191476 | A1 | 7/2012 | Reid et al. |
| 2012/0265265 | A1 | 10/2012 | Razavi et al. |
| 2012/0283794 | A1 | 11/2012 | Kaib et al. |
| 2012/0293323 | A1 | 11/2012 | Kaib et al. |
| 2012/0302860 | A1 | 11/2012 | Volpe et al. |
| 2012/0310315 | A1 | 12/2012 | Savage et al. |
| 2013/0085538 | A1 | 4/2013 | Volpe et al. |
| 2013/0144355 | A1 | 6/2013 | Macho et al. |
| 2013/0231711 | A1 | 9/2013 | Kaib |
| 2013/0245388 | A1 | 9/2013 | Rafferty et al. |
| 2013/0274565 | A1 | 10/2013 | Langer et al. |
| 2013/0317852 | A1 | 11/2013 | Worrell et al. |
| 2013/0325078 | A1 | 12/2013 | Whiting et al. |
| 2014/0012144 | A1 | 1/2014 | Crone |
| 2014/0025131 | A1 | 1/2014 | Sullivan et al. |
| 2014/0046391 | A1 | 2/2014 | Cowan et al. |
| 2014/0070957 | A1 | 3/2014 | Longinotti-Buitoni et al. |
| 2014/0163663 | A1 | 6/2014 | Poddar et al. |
| 2014/0324112 | A1 | 10/2014 | Macho et al. |
| 2014/0378812 | A1 | 12/2014 | Saroka et al. |
| 2015/0039053 | A1 | 2/2015 | Kaib et al. |
| 2015/0161554 | A1 | 6/2015 | Sweeney et al. |
| 2015/0182797 | A1* | 7/2015 | Wernow ................. G16H 20/30 482/8 |
| 2015/0297135 | A1 | 10/2015 | Shoshani et al. |
| 2015/0304478 | A1* | 10/2015 | Kim ....................... G16H 40/63 455/414.3 |
| 2015/0328472 | A1 | 11/2015 | Sullivan et al. |
| 2016/0004831 | A1 | 1/2016 | Carlson et al. |
| 2016/0076175 | A1 | 3/2016 | Rock et al. |
| 2016/0076176 | A1 | 3/2016 | Rock et al. |
| 2016/0082277 | A1 | 3/2016 | Foshee, Jr. et al. |
| 2016/0113581 | A1 | 4/2016 | Amir et al. |
| 2016/0256104 | A1 | 9/2016 | Romem et al. |
| 2016/0283900 | A1 | 9/2016 | Johnson et al. |
| 2017/0014073 | A1 | 1/2017 | Shoshani et al. |
| 2017/0027469 | A1 | 2/2017 | Amir et al. |
| 2017/0036066 | A1 | 2/2017 | Chahine |
| 2017/0040758 | A1 | 2/2017 | Amir et al. |
| 2017/0162840 | A1 | 6/2017 | Pendry |
| 2017/0281462 | A1* | 10/2017 | Freeman .............. A61N 1/0484 |
| 2017/0319862 | A1 | 11/2017 | Foshee, Jr. et al. |
| 2017/0323055 | A1* | 11/2017 | Gaffield ................. G16H 10/60 |
| 2017/0367591 | A1 | 12/2017 | Jorgensen |
| 2018/0116537 | A1 | 5/2018 | Sullivan et al. |
| 2018/0117299 | A1 | 5/2018 | Gustavson et al. |
| 2018/0184933 | A1 | 7/2018 | Sullivan et al. |
| 2018/0185662 | A1 | 7/2018 | Foshee, Jr. et al. |
| 2018/0243578 | A1 | 8/2018 | Volosin |
| 2018/0361165 | A1 | 12/2018 | Jaax et al. |
| 2019/0030352 | A1 | 1/2019 | Sullivan et al. |
| 2019/0076666 | A1 | 3/2019 | Medema |
| 2019/0116896 | A1 | 4/2019 | Armour et al. |
| 2019/0321650 | A1 | 10/2019 | Raymond et al. |
| 2021/0228893 | A1* | 7/2021 | Akram ................. A61N 1/3925 |
| 2023/0066525 | A1 | 3/2023 | Cabanas et al. |
| 2023/0123348 | A1 | 4/2023 | Mehta et al. |
| 2023/0336958 | A1 | 10/2023 | Mehta et al. |
| 2023/0410635 | A1 | 12/2023 | Katz et al. |
| 2024/0048952 | A1 | 2/2024 | Seidberg et al. |
| 2024/0114328 | A1 | 4/2024 | Mehta et al. |
| 2024/0144802 | A1 | 5/2024 | Beyer et al. |
| 2024/0267719 | A1 | 8/2024 | Pellegrini et al. |
| 2024/0276193 | A1 | 8/2024 | Martin et al. |
| 2024/0292201 | A1 | 8/2024 | Katz et al. |
| 2024/0334172 | A1 | 10/2024 | Bozik et al. |

FOREIGN PATENT DOCUMENTS

| | | | |
|---|---|---|---|
| JP | 2005507747 | A | 3/2005 |
| JP | 2014500099 | A | 1/2014 |
| JP | 2014526282 | A2 | 10/2014 |
| WO | 9839061 | A1 | 9/1998 |
| WO | 2011/146448 | A1 | 11/2011 |
| WO | 2012/064604 | A1 | 5/2012 |
| WO | 2012/151160 | A1 | 11/2012 |
| WO | 2015/056262 | A1 | 4/2015 |
| WO | 2023107404 | A2 | 6/2023 |

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi: 10.1093/eurheartj/eht167, European Society of Cardiology.

LIFECOR LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

Zoll, LifeVest, Proven protection from Sudden Cardiac Death, issued Mar. 27, 2018, 4 pages. Pittsburgh PA, USA.

International Search Report and Written Opinion for PCT Application No. PCT/US2015/051726, dated May 20, 2016, European Patent Office, Rijswijk, 11 pages.

* cited by examiner

LOCAL ACCESS TO SITUATION REPORTS USING A WEARABLE MEDICAL DEVICE

CROSS REFERENCES TO RELATED APPLICATIONS

This application claims the benefit of the filing date of U.S. Provisional Patent Application No. 63/446,486, filed Feb. 17, 2023, the disclosure of which is hereby incorporated herein by reference for all purposes This application is a continuation-in-part of U.S. patent application Ser. No. 18/544,397, filed on Dec. 18, 2023, the disclosure of which is hereby incorporated herein by reference for all purposes.

FIELD OF THE INVENTION

The present disclosure generally relates to generating adapted reports for use in caring for patients.

BACKGROUND

Frequently medical emergencies require that a patient promptly receive treatment to attain a positive outcome. Some wearable medical devices can monitor a patient as the patient goes about day-to-day activities. Along the way, the wearable devices can accumulate a plethora of information about the patient. In some cases, the wearable medical devices can also deliver treatment to the patient on the fly. Despite the health benefits of wearable medical devices, there is often additional need for human intervention to provide immediate care to the patient.

When a medical emergency happens while a patient is in the field away from a medical facility, a trained emergency support person, e.g., emergency medical service (EMS) person, may need to quickly evaluate the situation of the patient before tending to the patient. An emergency support person can gain valuable insight from information about the patient's current and previous situation to adapt care to the specific needs of the patient. For example, a description of treatment already dispensed by the wearable medical device to address a medical event can be important information.

In one example of such a medical event, a heart arrhythmia involves the heart ceasing to properly pump blood throughout the body. The malfunction can lead to collapse, unconsciousness, and death of the patient if not immediately treated. The longer the patient is in sudden cardiac arrest (SCA) or re-cardiac arrest, chances of survival goes down. The patient often becomes unconscious within 6 seconds. With every minute after an SCA, the chance of survival for the patient can incrementally decrease, as much as 10% per minute. For example, absence of oxygen for 2 minutes can lead to brain damage and if the absence lasts for more than 4 minutes, brain cells may be permanently lost. However, if oxygen supply is restored immediately, the patient can regain consciousness within seconds.

Treatment of sudden cardiac arrest (SCA) often involves resuscitation with CPR and defibrillation. A defibrillator device, such as an automated external defibrillator (AED) or a wearable cardiac defibrillator (WCD), can be used to deliver a therapeutic dose of electrical energy through the chest wall to the heart of the patient. This can often restart the heart and restore the heart's natural rhythm. With prompt treatment, SCA can be reversible and at times, lead to a successful recovery.

However, there may also be times that CPR is not recommended depending on the particular circumstances of the patient at the time. For example, if the patient has been already treated with a shock by a wearable device and is in normal sinus rhythm, then recovery treatment (such as oxygen) may be appropriate to be implemented, rather than CPR. Standard protocols are not always the care that a patient requires at the time. In such circumstances, equipping a support person with relevant information may ensure proper care is performed and the support person can know what correct equipment to bring to the patient.

SUMMARY

A medical support system (also referred to as "support system") is provided to facilitate prompt access to situation information by a trained support person who assists a patient experiencing a medical event that requires immediate attention. In some implementations, the medical support system may be applied for medical support as a cardioverter defibrillator (also referred to as a "cardioverter defibrillator support system or "wearable cardiac defibrillator" (WCD) support system). A wearable medical device (also referred to as "wearable device" or "wearable") gathers patient data that can be used in generating situation reports on the fly. The situation reports include critical health information regarding a patient for the medical event, such as lifesaving information regarding the circumstances of the patient prior to, during, and/or immediately after the medical event. Various short-range connection methods may be employed to quickly provide a trained support person with situation information to create and present the situation reports to the support person.

A method is provided that employs a medical support system, such as a cardioverter defibrillator support system, to provide local access to a situation report for assisting a patient. According to the method, a wearable medical device, such as a wearable cardiac device (WCD), that is worn by a patient gathers patient data. The wearable medical device (e.g., WCD) determines that the patient experiences a medical event, for example, one or more arrythmias, when the patient is away from a medical treatment site, based at least in part, on the patient data. Where a WCD is provided, defibrillation treatment may be initiated by the WCD for the one or more arrythmias, for example, triggered by determination that the medical event requires such a treatment based on the patient data.

At least a portion of the patient data is processed, e.g., by the WCD, to produce situation information associated with the medical event, including formatting the situation information for inclusion in the situation report. The wearable medical device, e.g., by the WCD, further establishes a short-range connection with a communication device of a trained support person and transfers the situation information to the communication device via the short-range connection during a critical time for care. The situation information is used to generate the situation report at the communication device. The situation report is useable by the trained support person to administer medical care to the patient.

In some implementations, to establish the short-range connection, an invitation is sent to the communication device to trigger launching of a reporting application on the communication device. The reporting application is employed to generate the situation report using the situation information. The situation information data can patient data related to the defibrillation treatment, if such treatment is performed. In some cases, the situation information is formatted to include indications in the situation information to specify which of one or more fields of the situation report the reporting application is to insert situation information. The situation information that is transferred may include a stream, e.g., electrocardiogram (ECG), of the patient data of a current patient state recently captured by the wearable medical device, WCD, and/or snippets, e.g., ECG, of a prior patient state previously captured patient data.

In still some aspects of the method, the short-range connection between the wearable medical device and communication device of the trained support person includes a BLUETOOTH Low Energy (BLE) connection. A connectable advertising packet may be broadcast by the wearable device including an alert about the medical event and availability of the situation report. At times, the BLE connection may be used to provide standard medical information in addition to patient-specific situation information. For example, a first universally unique identification (UUID) for the medical event, e.g., associated with arrythmia, may be transmitted to specify a service that includes receiving situation information. The same UUID or a second UUID may specify characteristics of the situation information, e.g., for arrythmia treatment.

Additional transmitted information may include patient spotting information including at least one of: patient location information and a physical description of the patient to assist in locating the patient.

In some configurations of the medical support system, such as a cardioverter defibrillator support system, a method is used that employs steps as described above and a BLE connection is established, for example by a wearable cardiac device (WCD), to provide access to situation reports in assisting a patient. A BLE advertising packet, receivable by the communication device, may be disseminated to advertise a medical event, such as one or more arrythmias, and availability of situation report associated with the medical event. A connection request response may be received from the communication device approving the connection to access to situation information. A one-to-one connection may be established with the communication device and the wearable medical device transfers in a BLE data packet via the one-to-one connection during a critical time for care, the situation information formatted for inclusion in the situation report generated by a reporting application running on the communication device.

In some cases, the BLE connection may be bidirectional, where a request for particular additional situation information may be received from the communication device. In response, the wearable medical device may transfer in one or more additional BLE packets, the additional situation information.

In some instances, the situation information may include x and y coordinate data for the reporting application to create an ECG for display on the communication device.

In some implementations, medical support system, such as a cardioverter defibrillator support system, is provided, which is configured to provide local access to a situation report for assisting a patient. The medical support system includes a wearable medical device, such as a wearable cardiac device (WCD) to be worn by the patient when in use. The wearable device includes one or more sensors to collect patient data associated with the patient. A patient assessment module is also included to determine that the patient experiences a medical event, based at least in part on the patient data. In systems that include a WCD, a treatment unit may also be provided to administer defibrillation treatment of the one or more arrythmias. Further to the wearable device components, an interface is provided for establishing a short-range connection with a communication device of a trained support person in response to determining the medical event.

The medical support system also includes one or more processors and logic encoded in one or more non-transitory media for execution by the one or more processors and when executed operable to perform various operations as described above in terms of the method including transferring the situation information to the communication via the short-range connection during a critical time for care to generate the situation report. A situation information module processes at least a portion of the patient data to produce situation information associated with the medical event experienced by the patient when the patient is away from a medical treatment site. The situation information is formatted for inclusion in the situation report.

The medical support system may include a reporting application for use by the communication device. The reporting application may be configured to generate the situation report incorporating the situation information received from the wearable medical device. In some instances, the reporting application may be configured to translate x and y coordinate data from the received situation information into graphic representations on an ECG for display on the communication device. The situation report is configured for use by the trained support person to administer medical care to the patient according to the situation information.

This summary is not intended to identify key features of the claimed subject matter, nor is it intended to be used as an aid in determining the scope of the claimed subject matter.

BRIEF DESCRIPTION OF THE DRAWINGS

Various implementations in accordance with the present disclosure will be described with reference to the drawings.

DETAILED DESCRIPTION

Figure 1:
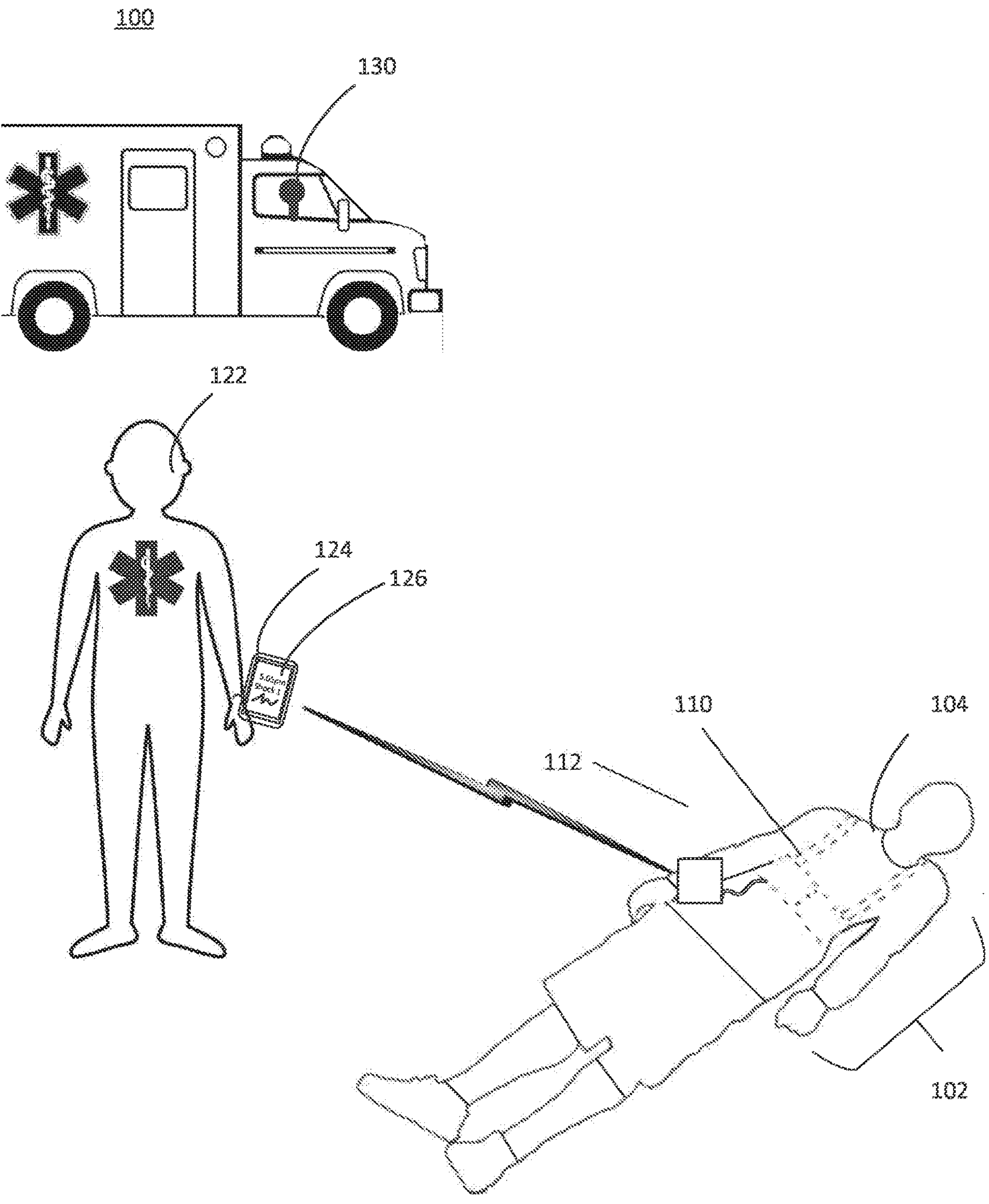
FIG. 1 is a conceptual diagram of an example of the medical support system employed to assist a trained support person in caring for a patient experiencing a medical event, in accordance with some implementations.

In the following description, various implementations will be described. For purposes of explanation, specific configurations and details are set forth in order to provide a thorough understanding of the implementations. However, it will also be apparent to one skilled in the art that the implementations may be practiced without the specific details. Well-known features may be omitted or simplified without obscuring the implementations described. The description of the medical support system provides a framework which can be tailored to individual systems built around the medical support system. Elements may be described in terms of "basic functionality" or varying degrees of functionality.

The present medical support system presents situation reports to a trained support person at the scene of patient experiencing a medical event in the field. The medical support system alerts the trained support person of the medical event occurring near to the trained support person. The support system further provides rapid and convenient transmission of relevant situation information about the patient, medical event, and/or treatment to the trained support person to assist in administrating appropriate care to the patient. For example, the situation report may be accessed by the trained support person prior to visual or physical contact with the patient to know what rescue equipment the trained support person needs to bring to the site of the patient. The medical support system may provide to the trained support person personalized instructions or suggestions on care of a patient to implement rather than standard treatment protocols that, at times, may not be recommended for a patient under certain circumstances. The medical event can be an emergency that poses an immediate risk to the health, especially the long term well-being, or the life of the patient.

A wearable medical device of the support system includes a wearable article worn by the patient. The wearable medical device gathers patient data from which the situation reports are generated. The patient data may include various data related to occurrence(s) associated with the medical event. The occurrences may be episodes of the medical event occurring close in time, environmental happenings around the time of the medical event, actions, or state of the patient before, during or after the medical event, detection of various patient physiological parameters (such as a glucose level for a patient with diabetes), etc. The support system processes the patient data that relates to the medical event, including specific occurrences associated with the medical event, to produce situation information. For example, various situation factors may be used to extract from the patient data, the situation information associated with the medical event. Prior to transferring the situation information to the communication device of the trained support person, the situation information is formatted to be translated into a situation report by a reporting application at the communication device. The resulting situation report is output to the trained support person.

At times, the patient may experience multiple related medical events, which may be connected by time of the occurrences falling within an event time period, cause and effect, various medical effects stemming from a common cause, or other relationships. For example, a medical event of a patient falling may be a result of another medical event of a cardiac episode. Situation information provided in the situation report may be associated with each individual related medical event and/or a relationship between medical events. In some implementations, situation information may provide occurrence times of or between various related medical events and/or time of or between treatments for the related medical events or occurrences.

Typically, a situation report may be generated on the fly using patient data that is gathered in real time by the wearable device. The situation report may also include standard predefined information for a given medical event. For example, a registered universally unique identification (UUID) may be associated with the particular medical event and service of providing the situation report. This medical event UUID or a second UUID may specify standard protocols to care for a patient experiencing the particular medical event. In such instances, the standard care information may be merged with the processed situation information and presented to the trained support person in the situation report. The situation information specific to the patient may override the standard care information, especially in cases that the situation information contradicts the standard care information. For example, where CPR is standard protocol but is not recommended for the particular patient medical event, the situation report may present a warning that CPR should not be performed.

In some implementations, the situation report may be adapted to the type and/or degree of assistance that is currently available for the patient. For example, situation reports may be tailored according to a level of expertise of any given support person, such as an extent of experience and/or training of the support person. In some instances, the wearable device may receive identifying information from the communication device that indicates a level of training of the support person. In some implementations, the trained support person may be previously authenticated to determine a level of detail for the situation report. The situation report may also be adapted according to accessibility of resources including medical equipment located near the support persons at the scene.

Situation information may reflect the situation of the patient immediately prior to the medical event, during the medical event, and/or immediately after the patient experiences a medical event. In some implementations, the situation information may include characteristics of the medical event, characteristics of treatment provided or anticipated to be provided to address the medical event, environmental conditions, patient context information, such as patient history, known ailments, activities performed by the patient prior to the medical event, and other patient context details relevant to patient care, etc.

Access to situation reports may be controlled by a reporting software application (referred to as "reporting application") that runs on the communication device of the trained support person, enabling authorized communication with the wearable medical device to receive and situation information and incorporate the situation information into the situation report.

The term "patient" as used in this description refers to a person who experiences a medical event or is suspected of experiencing a medical event. A "medical event" is a medical related problem or occurrence detectable by the wearable medical device and for which time sensitive care is required. For example, a medical event related to cardiac conditions may include ventricular tachycardia (VT), ventricular fibrillation (VF), bradycardia, supraventricular tachycardia (SVT), atrial fibrillation (AF), asystole, and non-sustained ventricular arrhythmia episodes, etc. Occurrences associated with a medical event may include a physical happening that is part of the medical event, such as an arrythmia, may include a variety of circumstances such as a symptom of a medical condition associated with the medical event, a status or action of the patient related to the medical event, an environmental condition effecting the medical event, and may also include a treatment provided, such as via the wearable device, to address the medical event.

The medical event can initially be detected at a physical location of the patient, which is typically a non-medical treatment site. For example, the patient may first experience the medical event while in a public place away from a medical treatment site, then be transported in a medical emergency vehicle, and arrive at a medical treatment site, such as a hospital. Thus, the term "patient location" of the medical event can include one or more physical locations. Various support persons in a chain of care at any of these patient locations may use the medical support system to gain valuable knowledge of the situation of the patient and multiple situation reports can be adapted to the different support persons and/or resources available at any given time along the chain of care.

The "trained support person" or "rescuer" for purposes of this description, refers to a person who had been previously formally trained in medical techniques to professionally address the type of medical event of a patient. A trained support person can include an emergency medical technician (EMT), emergency room staff, doctor or other formally trained persons who are with the patient at the scene of the medical event at the time of or immediately after the medical event during the critical time for care.

Typically, the trained support person and/or an organization of the trained support person is/are registered with the medical support system. Such controlled access may enable a trained support person to gain access to a high (second) tier situation report that includes patient sensitive information, complex medical details, instructions on care that only a trained professional can perform, and other situation information appropriate for a trained and/or preapproved trained support person. The situation information may be instrumental in the trained support person making treatment decisions for the patient. Controlled access via a reporting application on a communication device of (in possession of) the trained support person may include Bluetooth Low Energy (BLE) communication connection or other short-range communication connections with the medical device as described below. Additional tiers of situation reports are possible depending on the training level and/or authorization level of the trained support person. In some circumstances, a patient may provide pre-approval for any trained support person to access patient sensitive information during an emergency and the situation reports may include patient sensitive information accordingly.

A "critical time" for care can be any length of time after the onset of a medical event during which care of the patient may critically effect the outcome for the patient. For example, for a patient suffering from SCA the critical period may be just minutes before an irreversible health outcome happens to perform CPR treatment. The medical support system is configured to provide situation information to generate a situation report within the critical time for care of a patient.

In some implementations, a rapid communication connection may be established to transfer to a trained support person situation information that enables generating and viewing of the situation report saving precious seconds. Use of such rapid communication connections could be faster for automatically obtaining information upon the wearable device detecting a medical event, than manual data requests, such as a user calling into a medical system to request patient data.

The rapid communication connection may be a short-range wireless connection, for example, that uses radio waves as a communication medium, such as BLE (e.g., data broadcast or point-to-point). The short-range connection may also include near field communication (NFC), infrared communication (e.g., irDA), radio-frequency identification (RFID), communicating the link with Zigbee transmission, ultra-wide band (UWB) transmission, Z-wave transmission, Thread network, use of acoustic encoded patterns or other audio data transmission techniques including audible data, and other rapid proximity-based data transfer techniques for data transfer between the wearable medical device and the communication device of the trained support person. The short-range connection may transfer data at or near the patient, for example, within 100 meters, or can be as short as 4 cm for NFC, 30 m for BLE, etc., depending on the communication technology employed. In some implementations, the short-range communication of situation information for situation reports may be supplemented with cellular communication of some situation information, such as the wearable device sending basic situation information via a text message to a trained support person's cellphone number. Such cellphone number of the trained support person may be retrieved as a support person identifier when establishing the short-range communication between the communication device and the wearable device.

Some communication connections may rely heavily on energy resources for a radio to be constantly turned on. For example, a communication device scanning for classic BLUETOOTH connections may be continuously working to scan numerous radio frequency (RF) channels for medical alert signals, consuming much battery resources. However, the communication device using the reporting application enabled for BLE connections, for example, may need to scan just a few RF channels (e.g., 3 channels) to detect a medical event alert. Furthermore, A radio transmitter of a BLE enabled wearable device may conserve power by maintaining an idle radio state until activated to broadcast advertising packets in response to detecting a medical event. In this manner, detection of the medical event serves as a trigger to awaken the radio, reserving power of the wearable device for use when necessary to connect with a communication device of a trained support person. Idle times can help with battery recovery. Classic BLUETOOTH may pose privacy risks that can be avoided with BLE and use of a registered reporting application.

For illustration purposes, FIG. 1 depicts an example use case of the medical support system 102 in which a patient 104 suddenly experiencing a medical emergency at a non-medical treatment site 100. The medical event is detected by a wearable medical device 110 including a medical article worn by the patient 104. The medical event requires rescuer(s) action to help the patient. In this illustration, the patient suffers an SCA. In other cases, various different medical events may be experienced by the patient 104 and assisted by the medical support system 102.

According to this example, a local rescuer 122 is near the scene of the medical event and receives an alert on a communication device 124 sent from the wearable device 110 informing that a patient within the vicinity of the rescuer is in need of care. The local rescuer 122 is not initially aware of the circumstances of the patient 102 or any treatment that might have been provided by the wearable medical device. Without such background information, care for the patient would be limited and delayed. The rescuer gains the needed information in a situation report and is able to perform appropriate actions.

In this illustration, the medical support system transmits an alert such as by a main unit 112 of the wearable device 104 via a short-range broadcast to communication device 124 of the local rescuer 122 letting the local rescuer 122 know the particular medical event the patient is experiencing. The alert may include an invitation to the communication device to launch a reporting application and engage with the wearable device.

The rescuer communication device 124 may be a smartphone, smart watch, specialized medical device, such as a defibrillator enabled for communication with the wearable medical device, etc. For example, a defibrillator carried by a trained support person may have the reporting application preinstalled and capability of communicating with the wearable device.

At times, a rescuer may have a particular level of expertise in addressing the type of medical event experienced by the patient. Authentication for accessing a particular tier of situation information may be preestablished for the trained support person and provided via a reporting application running on the communication device of the trained support person. In some implementations, the level of expertise information may be transmitted from the communication device to the wearable device to indicate the tier of situation information appropriate for the rescuer to access. A situation report may be adjusted based on the level of expertise to access a particular tier of situation information. For example, only situation information associated with a particular tier level may be provided to the authenticated trained support person. The low tier situation information may exclude patient personal information, such as person identifying information, and other sensitive information regarding the patient. Further excluded from low tier information may be medical details that require a highly trained professional prepared for the medical event.

A situation report may include situation information about occurrences related to the medical event, for example, basic details about the medical event, treatments being performed by the wearable medical device, basic life support instructions, etc. In some implementations, the situation information may include patient specific information, for example, critical information in view of the medical event and/or patient. For example, where a preexisting condition of the patient renders certain actions deleterious for the patient, such as an allergic reaction or actions that may negatively implicate secondary medical conditions of the patient, the rescuer may be warned not to perform such actions. Where basic care is critically necessary for the particular patient, such as use of an EpiPen or providing a sweet food to address a diabetes attack, the rescuer may be instructed to perform including instructions on the steps needed to perform the critically necessary basic acts accordingly.

If a treatment episode has recently been delivered or is about to be delivered to the patient by the wearable medical device to address the current medical emergency, the situation information may notify the rescuer of the treatment episode. For example, should a shock treatment still be required, the screen depicts situation report information to inform the rescuer that a shock treatment will be delivered to the patient and to stand clear. The wearable medical device may then deliver a therapeutic shock to the patient and the medical support system then informs the rescuer that CPR can be initiated, such as providing instructions for chest compressions and recue breaths.

High tier situation information can include patient sensitive information. For example, high tier situation information may include identifying information to identify the patient and other patient-specific personal information, such as name, address, medical history including prior medical events and other medical conditions of the patient, emergency contact, advanced characteristics of the medical event detected by the wearable device. High tier information may also include patient context information for details of the patient within an event time period considered relevant to the particular medical event. Patient context information may include, for example, occurrences of: patient activity prior to the medical event, a prior patient activity level (such as high heart rate exercise), a type of prior patient activity (such as a type of exercise), a prior location of the patient, a patient current state or prior state (such as hydration level, time since last meal, lack of sleep, stress level, etc.), one or more current and/or prior vital signs or other physiological parameters of the patient, and combinations thereof, etc. It should be understood that various tiers of detail may be applied to situation information selected to be transmitted to the support person. The examples of low/high tiers are described herein for illustration purposes.

In some implementations, select vital sign data, such as vital sign data associated with a particular time or corresponding with other patient detected events, may be extracted from streamed medical data, such as stream of electrocardiogram (ECG) data. The stream of medical patient data may be continuously captured and collected via sensors of the wearable medical device. In other implementations, the patient data may be captured at defined intervals or upon triggering of an event, such as snippets of ECG data (representing a defined period of time). Patient context information may also include a comparison of patient data of the patient.

There can be important advantages to the present medical support system 102 alerting local rescuers of the medical event via short-range communication prior to a dispatched rescuer 130 arriving. Other prior medical alert systems may depend on an emergency call (e.g., 911 call) to be placed by an observer on-site with the patient or by the patient making the call. These prior systems are further restricted in the substance of information provided to emergency persons, relying on a limited description of an untrained observer or the patient. Often, the patient or an observer are not accessible to provide such descriptions.

In the illustration in FIG. 1, a dispatched rescuer 130, may subsequently arrive on the scene after the local rescuer 122, in response to long-range communication alert (e.g., 911 call to a dispatch center), such as an EMS rescuer assigned by an emergency service to travel to the scene of the emergency to transport the patient 104 to a medical care facility. Valuable care may have already been provided by the local rescuer 122. Once the dispatched rescuer 130 is within the short-range communication area, the dispatched rescuer 130 may also pair with the wearable device and receive situation information to generate a situation report. The present support system may provide patient specific information to a trained support person very quickly, at times prior to an information dispensing service, such as Global Medical Response (GMR) action. Without the situation information provided by the support system, crucial time would be taken by the EMS rescuer 130 in assessing the situation of the patient before tending to the needs of the patient.

Benefits of the medical support system include improving patient care by a trained support person. Proactively providing of situation report information may reduce the time for a diagnosis, free up more time for care, and allow for appropriate treatment specifically tailored to the medical event and patient situation.

Some implementations of the medical support system may additionally present instructions for appropriate actions by a trained support person, especially in cases that the patient has specific issues that may make one treatment favorable over another treatment, or if a commonly applied treatment is not favorable due to issues of the patient. The trained support person may not be aware of that the wearable medical device may deliver a treatment that requires careful interaction by the trained support person. For example, a wearable medical device that delivers a shock could injure the trained support person if touching the patient. In another example, a patient may have psychological disturbances that may be aggravated if the trained support person interacts with a conscious patient in a particular manner.

Figure 2:
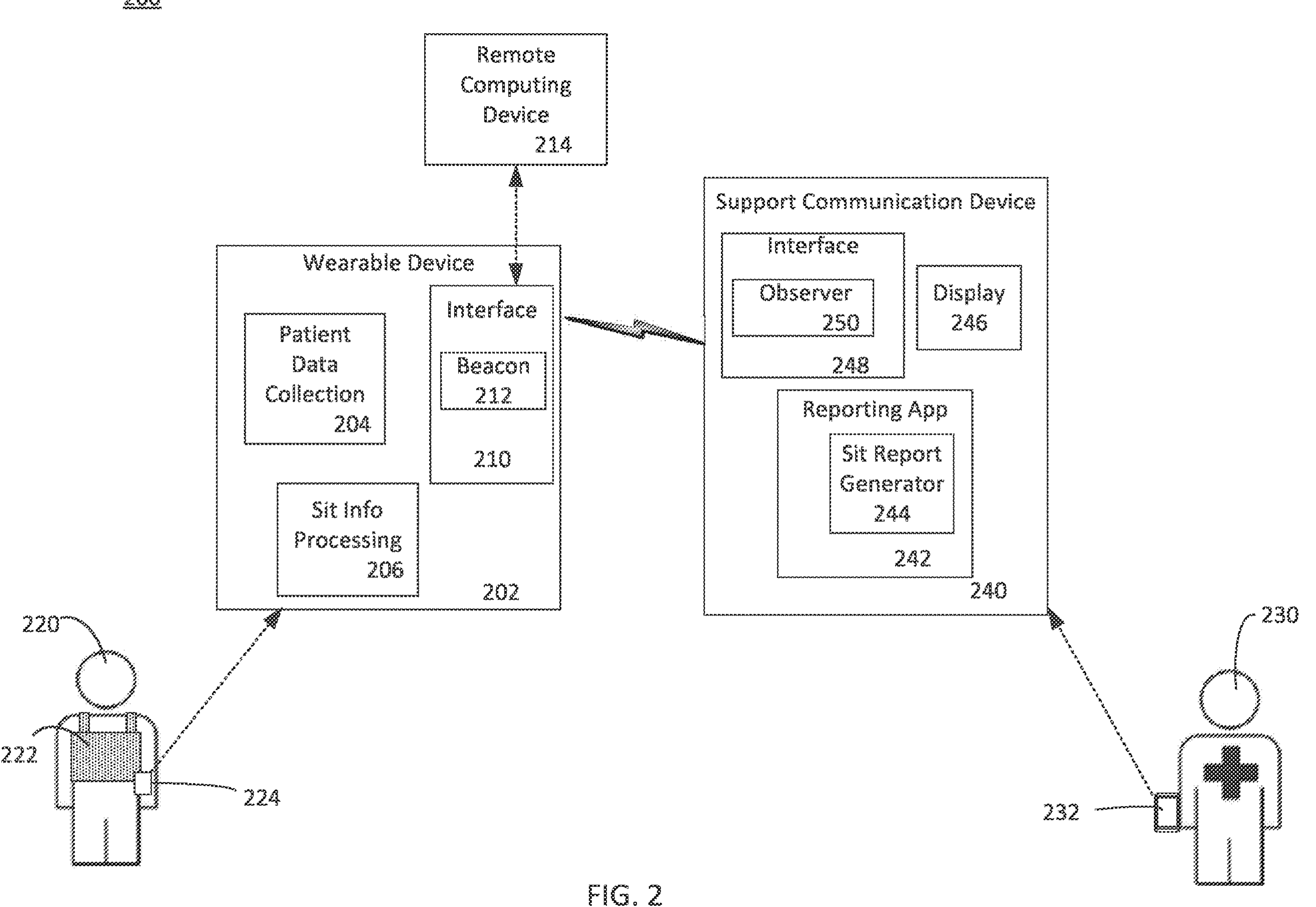
FIG. 2 is a block diagram of example of the medical support system including a wearable medical device that transmits situation information to a communication device of a trained support person, in accordance with some implementations.

FIG. 2 shows the medical support system 200 having a wearable medical device 202 (shown by way of a block diagram with components) including a wearable medical article 222 that is worn by patient 220 and a communication device 232 (shown by way of a block diagram 240 with components) of a trained support person 230, which interact over a short-range connection 260. The wearable medical device may further communicate with one or more remote computing devices 214.

The medical support system 200 refers to one or more physical devices and also includes software components. The wearable medical device includes functional computing components, such as one or more processors, one or more memories, interfaces, operating system, computer programs, etc., similar or the same as such computing components described regarding the examples of wearable medical devices 800 in FIGS. 8 and 900 in FIG. 9.

Particular implementations of various computing components of the medical support system may be implemented in a computer-readable storage medium for use by or in connection with the instruction execution system, apparatus, system, or device. Particular embodiments can be implemented in the form of control logic in software or hardware or a combination of both. The control logic, when executed by one or more processors, may be operable to perform that which is described in particular implementations. For example, a non-transitory medium such as a hardware storage device can be used to store the control logic, which can include executable instructions.

Some examples of a wearable medical device 202 include a wearable cardioverter defibrillator (WCD), such as the ASSURE wearable defibrillator system available from Kestra Medical Technologies, Inc., Kirkland, WA. Other WCD devices are possible for use in the medical support system. A WCD may also provide pacing therapy for detected bradycardia and/or asystole. The wearable medical device may further include monitoring devices that check patient parameters with or without integrated treatment components, such as Wearable Cardiac Monitoring system (WCM) by Kestra Medical Technologies, Inc., Kirkland, WA, Holter type of monitors, mobile cardiac outpatient telemetry (MCOT) systems by Philips Company, etc. Other wearable medical devices may be employed in the medical support system to address a variety of medical events and medical conditions. An example wearable medical device is described below with regards to FIGS. 8 and 9.

The wearable medical device 202 includes a wearable medical article 222 (also known as a wearable article or support structure) worn by patient 220 when in use. The wearable article 222 can be implemented in many different ways. For example, it can be implemented in a single component or a combination of multiple components. In embodiments, the wearable article 222 could include a vest, a half-vest, a garment, etc. In such embodiments such items can be worn similarly to analogous articles of clothing. In embodiments, the wearable article 222 could include a harness, one or more belts or straps, etc. In such embodiments, such items can be worn by the patient around the torso, hips, over the shoulder, etc.

In embodiments, wearable article 222 can include a container or housing. In such embodiments, the support structure can be worn by being attached to the body of the patient by adhesive material, for example as shown and described in U.S. Pat. No. 8,024,037. The wearable article 206 can even be implemented as described for the support structure of U.S. Publication No. US2017/0056682, which is incorporated herein by reference. A person skilled in the art will recognize that components of the wearable medical device 202 can be in the housing of the wearable article 222, for example as described in the U.S. Publication No. 2017/0056682 document, or external to the wearable article, such as main unit 224 attached to the wearable article 222, or other computing device of the patient, such as a smart phone, that is in communication with the wearable device. The wearable article 222 may also include other forms of wearables such as a headgear, wrist band, ankle band, etc. There can be other examples as well.

Software components of the wearable medical device 202 include a patient data collection module 204 to compile patient data generated and/or collected by the wearable medical device 202 and a situation information processing module 206 to process patient data and format situation information for use in a situation report. The patient data collection module 204 and situation information processing module 206 may be implemented as software components stored in a memory of the wearable medical device 202. Other wearable device components may include one or more connection interfaces 210 (such as an interface port) for the wearable device to interface with a communication device of the trained support person. In some implementations, at least some of the functions of the patient data collection module 204 and/or situation information processing module 206 may be performed at a remote computing device 214 in communication with the wearable medical device 202.

Patient data may be regularly collected or generated by the wearable medical device 202 while the patient goes about day-to-day activities. This patient data is assembled by the patient data collection module 204 and may be transfer to the remote computing system 214. In some implementations, the patient data may be transmitted from the remote computing system 214 to a medical professional at a medical facility for follow-up patient care. Patient data is associated with the health of the patient and typically includes data related to the current medical event (e.g., situation information), as well as other data unrelated to the medical event.

Some patient data may be generated by the wearable medical device 202 by a variety of sensors that may be integrated with or connected to the wearable medical article 222 or otherwise in communication with the wearable medical device. Examples of patient data from sensors or devices integrated with or in communication with the wearable device may include patient circumstances data, such as ECG data by electrodes of the wearable device, temperature of the patient and/or environment of the patient by a thermometer, peripheral capillary oxygen saturation (spO2) of the patient by an oximeter, step count data for the patient; respiration data measured by the wearable device; pulse ox data measured or collected by the wearable device, accelerometer data, which can indicate, for example, that the patient has fallen, or has been unconscious for a significant period of time, time records by a clock, a global positioning system (GPS) to indicate patient location and prior travel routes, etc. Patient data may also include characteristics of the medical event, such as description of a fall, nature of a seizure, etc. Details about various sensors of the wearable medical device 202 is described below with regards to FIG. 5. There can be other types of patient data generated by the wearable device from other types of sensors or detection device sources.

Patient data generated by a wearable medical device may include data related to treatment/therapy provided by the wearable device or diverted (e.g., initiated by the wearable device but failed to be provided to the patient) for the current instance of the medical event. For example, patient data may include asystole, description of types of treatment actions, e.g., shock deliveries and timing/number of treatment actions pacing deliveries, non-performed treatments due to diversion by the patient (e.g., the patient overriding the commencement of the treatment), etc.

Some patient data may be received by the wearable medical device 202 from sources external to the wearable device 202, such as remote computing system 214. Some of this patient data may be tangentially related to the medical event and relevant as situation information for a use by the trained support person. Patient data from external sources may include patient history data, such as from previous medical events of the patient, other patient conditions, disabilities, and/or characteristics, patient emergency contact, cautions that certain treatments are to be avoided for the particular patient, location tracking data, etc. The patient data may also be received from other external data repositories, data entered by a person, such as a medical professional, contact person of the patient, etc.

In some implementations, the wearable medical device 202 may regularly transfer patient data to remote computing system 214, such as transferring the data at a prescheduled time. In some implementations, the patient data may be transferred according to a trigger event, such as detection of the medical event by the wearable medical device 202. Such trigger event may include the patient data collection module 204 or other alert module of the wearable medical device causing the transmission of the patient data. In some implementations, transfer of patient data may occur according to a manual request, such as the patient activating a send command. In some medical support systems, any or all of the foregoing transfer techniques may be employed.

Data may be transferred between the wearable medical device and remote computing device via a network, such as e one or more WANs (Wide-Area Networks) and/or LANs (Local-Area Networks), which may be wired and/or wireless. In some examples, the network may include the Internet and/or one or more cellular networks, among other networks. For example, the network may provide a connection, for example, through a local network to a host computer or to data equipment operated by an Internet Service Provider (ISP). The ISP in turn provides data communication services through the worldwide packet data communication network (the "Internet").

The remote computing device 214 can be a server or other portal. An example of such a remote computing device 210 is KESTRA CARESTATION, from Kestra Medical Technologies, Inc., Kirkland WA. The remote computing system 210 may be implemented as a server, or using a web service such as, for example, Amazon Web Services (AWS) available from Amazon or Azure available from Microsoft. The remote computing device may also include multiple computer devices, such as on a cloud system, in which tasks may be distributed between computing device. In some cases, a patient location, such as a GPS location of the patient, may be published by the wearable device to a service that monitors for patients in needs of immediate patient care outside of a medical facility. Such patient monitoring computing devices may coordinate with the remote computing device and/or wearable device. Thus, the term "remote computing device" may include one or more computing devices that are remote from the site of the patient and work to support generation, availability, and access of the situation report.

Transfer of the patient data to the remote computing device 214 may occur using any of a variety of data communication mechanisms. At times, the wearable medical device 202 transmits the patient data to the remote computing device 214 via a wireless communication link, e.g., WiFi or cellular, to a patient computing device or main unit 224. The patient computing device may be a dedicated device for the sole use or major use in the medical support system. In other implementations, the patient computing device 216 may be a general device, such as a mobile phone, which includes software configured to transfer patient data to the remote computing device or some intermediary device that then transfers the patient data to the remote computing device 214. In still some implementations, the main unit 224 may be integrated in the wearable medical device 202 and include wired communications with the processor and memory of the wearable device 202 to transmit patient data to the remote communication device 214.

Processing of the patient data by the situation information processing module 206 to create situation information configured for a situation report for a medical event may include extracting, summarizing, reformatting patient data, etc. The patient data may be raw data detected by sensors of the wearable device and scanned by the situation information processing module 206 to extract only portions that are relevant and potentially helpful for a trained support person in care of the current medical event.

Such relevant information may include characteristics of the medical event, characteristics of any treatment already provided or soon to be provided by the wearable device, characteristics of the patient, instructions on how to care for the patient, warnings on actions not to be taken or needed to be taken by the trained support person, etc. For example, situation information related to a cardiac arrythmia event may include an onset time for each of the arrhythmias, a duration of each of the arrhythmias, a number of shocks delivered, a number of arrhythmias within an event time period, a type of each of the arrhythmias, and combinations thereof. Situation reports include data extracted from or otherwise processed based on the patient data that is determined to be relevant to the current medical event by meeting one or more situation factors. In some cases, a pattern of the patient data may be identified as an indication of pertinent situation information to assist in caring for the patient. Such situation information may be critical to treatment provided by the trained support person. For example, if a certain number of shocks have already been provided by the medical device, the trained support person may opt to provide alternative treatments to the patient. In another example, if the situation information indicates that the wearable device is prepping for a shock the trained support person may opt to hold off on performing CPR or deviate from other standard protocol based on the situation report.

The situation factors used in the processing of the situation information may depend on characteristics of the medical event, e.g., type of event. For example, situation factors may include an event time period relative to the medical event, identification of conditions that are known to induce or aggravate the medical condition, past patient history, etc.

The event time period may be defined according to the type of medical event and/or characteristics (e.g., patterns of behavior) of the patient to include a stretch of time applicable to the occurrence(s) of the medical event. For example, a diabetic medical event may be associated with an event time period of hours or a day to include food consumption. In this example, if a patient characteristically eats at particular times, the event time period may be defined accordingly. By contrast a cardiac medical event may have a shorter event time period to encompass more of the immediate happenings of the patient. For example, situation information may be extracted from ECG patient data for each medical event represented in the ECG data that meets threshold criteria for the event and results in an episode being opened. Some examples of recording of medical event episodes is described in U.S. Publication No. 20230091743, "Health Data Management and Display" filed Sep. 22, 2022, the contents of which is incorporated herein by reference.

For example, the situation information processing module 206 may create a summary of a medical event from extracted patient data to include characteristics of the medical event, e.g., arrhythmias, such as the number and/or types of each occurrence of the current medical event, e.g., each arrhythmias of detected, the time and duration of each detected occurrence, etc. In some implementations, location tracking data may be used in the situation information processing to map the path or route the patient traveled just prior detected medical event. Step count data during a predefined prior period of time before the detected events may be assessed as an indication of whether the patient was active or inactive just prior to detected events.

In some implementations, the situation information processing module 206 may be configured to analyze the received patient information to extract the event times, event summaries, ECG data for episodes, accelerometer, pulse ox, step count, patient location tracking maps, etc. of the patient just prior to detected events. Processing of the patient data to create the situation report may also include de-identifying the data to prevent access by support persons not authorized to access the identifying information.

In some implementations, the situation information processing module 206 can be configured to analyze the received patient data to determine appropriate actions for the current medical event and provide prompts or pointers to prompts for these actions. In some embodiments, each medical event type may serve as an index to a look-up table, library, or other database, that contains predetermined support prompts for various types of medical events. For example, support prompts could include instructions for performing CPR, providing a "metronome" for the CPR compression rate, positioning the patient to help prevent the patient from entering shock, check for bleeding, for example if a patient fall was indicated by the patient data, etc.

The situation information processing module 206 may also incorporate a care artificial intelligence (AI) component to learn and predict proper instructions for care of patients exhibiting particular combinations of characteristics, patient data, and conditions. The care AI component may also use patient history data of the subject patient to factor in past medical events of the subject patient and the procedures that resulted in favorable or non-favorable outcomes.

The situation information processing module 206 also formats the situation information for easy inclusion in a situation report at the receiving end of the communication device 232 of the trained support person 230. In some implementations, the situation report includes one or more fields for entry of the situation report. The situation information may be formatted by inserting indications to specify one or more fields of the situation report for inclusion of the situation information by a reporting application 242 of the support person communication device 240. The situation report may also be configured in a form for transmission and receipt by the communication device. For example, communication packets or signals may be encoded with the situation information.

The wearable interface 210 includes mechanisms for short-range communication with the support communication device 240, e.g., to support interface 248 Wearable interface 210 may include a beacon 212 to broadcast alerts to near-by trained support persons, which may be detected by an observer 250 when within transmission-receiving range. The observer 250 may be a feature of a generic application that scans for medical-related alerts, or may be a scanning application that is dedicated to the medical support system. In some implementations, when the observer 250 is within range of the beacon 212, the reporting application 242 may be woken up to prompt the user to input a decision to act (or input a rejection or ignore the alert) in response to the received alert. In some implementations, receipt of the alert may trigger a user prompt to accept or reject the situation report and acceptance by the user activates the reporting application 242.

The wearable interface 210 provides one or more short-range communication mechanisms for the trained support person 230 to access the situation report. The wearable interface 210 may facilitate short-range communication connections (for example, BLE, NFC, infrared communication (irDA), RFID, communicating the situation information with Zigbee transmission, acoustic or other audio data transmission techniques) with the communication device of the trained support person by formatting and encoding data into packets, signals, and other transmission modes.

In some implementations, the communication device 232 may also establish a long range communication connection with the remote computing device 214, e.g., to upload on-scene treatment information, follow-up with the regular physician of the patient, obtain technical services contact, etc.

The situation report generator module 244 at the communication device of the support person translates the received situation information to produce situation reports with the situation information. The report generation module 244 packages the situation information to show on display 246 in an easy to read structure to assist the trained support person 230 in caring for the patient. In some implementations, the situation report generator module 244 may use stored situation report templates and insert the situation information into appropriate fields in the situation report. The resulting situation report may include text, image(s) and/or video(s). Various views of the situation information may be presented, which may be automatically presented and/or certain views may be requested by the trained support person. For example, the trained support person may initially request a view of currently collected patient data followed by previous collected patient data.

In some implementations, situation information may be adapted to personal preferences of the trained support person. The reporting application 242 may employ a reporting artificial intelligence (AI) component to use previous behavior patterns of the trained support person to learn the type and order of situation information typically viewed by the trained support person. The reporting application may continually update attributes of the situation report, e.g., presentation, level of detail, and type of situation information, etc., based on the learning.

In some implementations, the report generation module 244 may be configured to determine from the situation information, the type of wearable medical device 202, for example from header data that the transmitting wearable medical device includes in the situation information. In such cases, a header attached before the payload may include a classification of the wearable medical device that describes the patient parameter(s) being monitored, treatment provided by the wearable device, product number, serial number, and/or other descriptive and identifying information. In some implementations, the reporting application may cross reference the header data with a type of medical device. The report generation module 244, based on the determined type, can generate a situation report file appropriate for the type of wearable medical device. For example, a situation report file for a wearable device that solely monitors patient parameters would not include situation information related to treatment by the wearable medical device.

In some implementations, the situation report may be specifically adapted for a level of expertise determined for the trained support person. In these cases, the level of experience of a trained support person at the scene may be a factor used in the processing of the patient data. Various tiers of detail may be extracted from the patient data depending, at least in part, on the level of experience of a trained support person.

Often, the situation report is visually shown on a display 236. In some implementations, other formats of situation report may include a hands-free verbal recitation of the situation report. In such circumstances, the reporting application 242 can provide interactive access to situation information in which the trained support person 232 may request via a microphone particular information from the wearable device and the reporting application receives the requested information and outputs the requested situation information through a speaker of the support communication device 232. The reporting application 242 can be implemented using a software module stored in a memory of the support communication device 232 and executed by one or more processors of the support communication device 232.

The access module 206 can implement various mechanisms for the trained support person to access the situation report. In some implementations, BLE packets may be dispersed upon detection of a medical event and the communication device 232 may receive the BLE communication to establish a rapid communication connection with the support system The depictions in FIG. 2 is not to be construed as limiting components of the medical support system 200 and how the support system 200 is implemented. The medical support system 200 can be implemented in different ways with additional or less devices. For example, in some implementations, the wearable device may include treatment hardware and/or software to address the medical event, such as a WCD. In such implementations, the patient data may include information regarding treatment performed by the wearable device for the medical event and/or treatment anticipated to about to be performed for the medical event.

Figure 3:
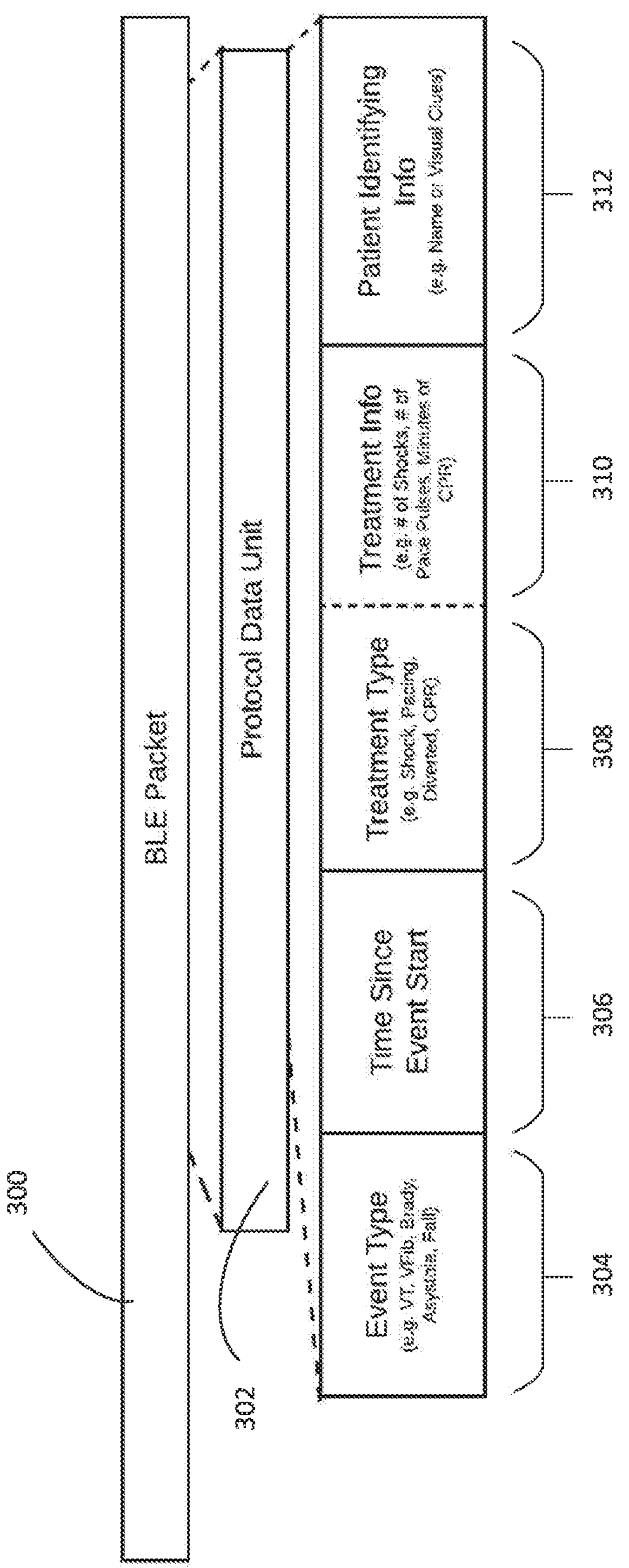
FIG. 3 is a block diagram of a BLE packet for situation information and patient identifying information, in accordance with some implementations.

FIG. 3 shows an example of a BLE packet 300 that includes formatted situation information encoded in a protocol data unit 302 of the BLE packet 300. Examples of situation information in the protocol data unit 302 may include medical event type 304 that is detected, and a time since the start of the medical event 306 or other time element to indicate when the patient experiences the medical event. Examples of medical event types may include a ventricular tachycardia (VT), ventricular fibrillation (VFib or VF), bradycardia (Brady), asystole, and a fall by the patient. Other medical event types are possible. The encoded situation information may also include treatment type 308 that can include treatments that had already been provided to the patient, or decisions to forego certain treatment. Examples of treatment types 308 may include shock treatment, pacing diverted and not provided, CPR, etc. Information regarding the treatment 310 may also be encoded into the protocol data unit 302. Examples of treatment information 310 may include the number of shocks provided, the number of pace pulses provided, the minutes of CPR provided, etc.

Figure 4:
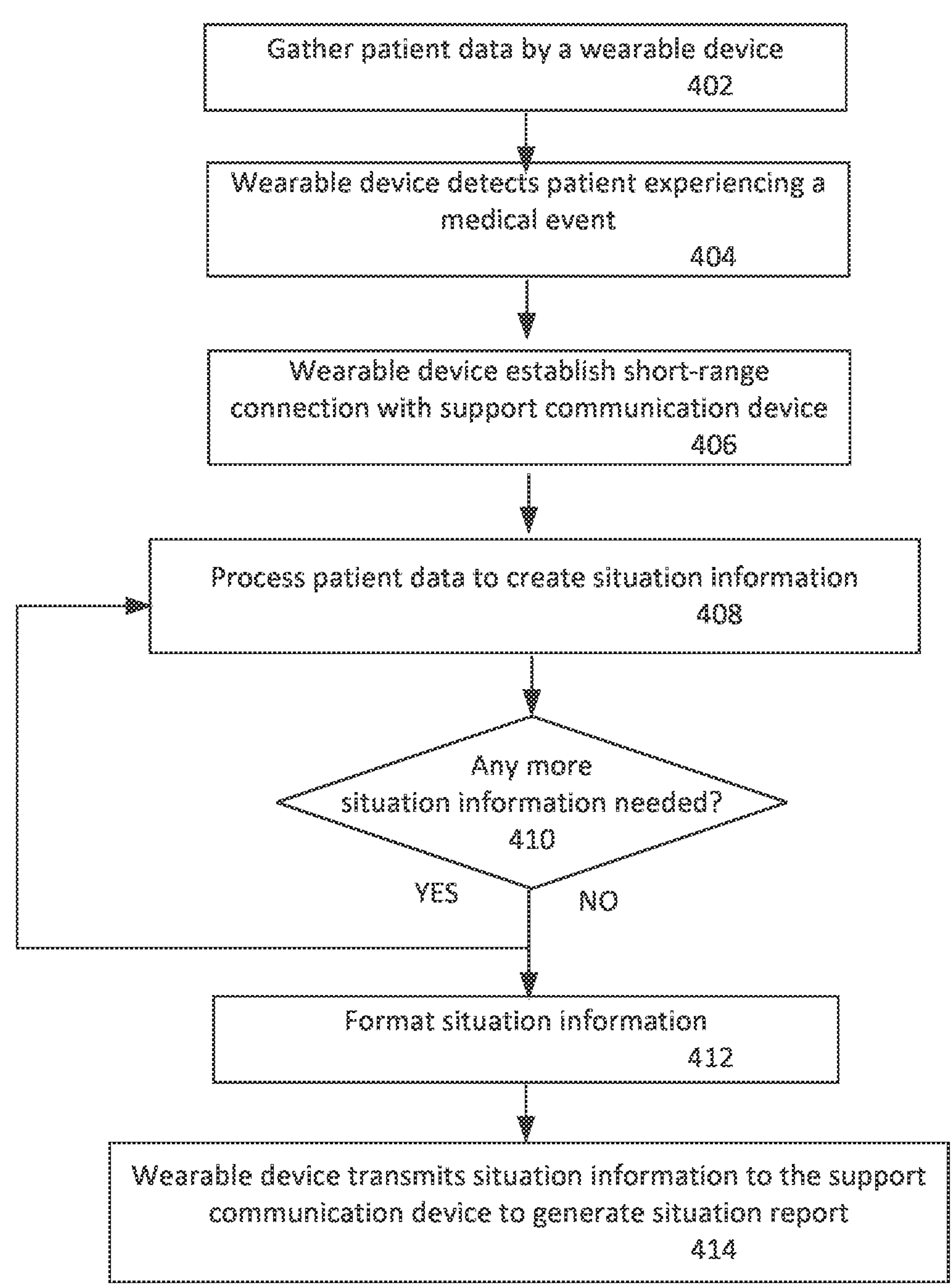
FIG. 4 is a flowchart of an example of a medical support process to provide local access to a situation report from patient data, in accordance with some implementations.

FIG. 4 shows a flowchart of an example medical support process 400 for the medical support system (for example, 202 in FIG. 2) to provide local access to a situation report for assisting a patient. The support process is often implemented on the wearable medical device (for example, 202 in FIG. 2). Certain steps can also be offloaded by the wearable medical device to various computing devices, such as an application running on a dedicated server, e.g., remote computing device, and/or an application hosted in the cloud. In implementations, the device or devices implementing the medical support process can be stand-alone or a combination of mobile processing and cloud processing. According to this description, the wearable device performs steps to connect with the support person and transfer situation information directly to the communication device of the support person.

In block 402, patient data are gathered, e.g., received from other sources or generated by the wearable device. Typically, patient data are routinely and automatically collected by the wearable medical device as the patient wears the wearable article. The patient data generally can relate to various aspects of the health of the patient and also include data relevant to the subject medical event. In this respect, patient data gathered by the wearable device may encompass health data unrelated to the subject medical event. The patient data thereby includes data associated with a time prior to the detection of the health event. Gathering of patient data further can continue after a medical event is detected (as in block 404 described below) and throughout some or all of the medical support process, as long as the wearable device remains worn by the patient or sensors of the wearable device remain activated.

The patient data may be a stream of recently acquired patient data by the wearable device that reflects a current state of the patient. The patient data may also include snippets or blocks of data captured during a specific previous period of time to indicate a prior state of the patient (e.g., prior to the trained support person accessing the situation report or arriving at the scene). In some implementations, a portion of the patient data (but not all the patient data collected) may be gathered in response to detection of the health event. For example, specific sensors may be activated upon detection of the health event and patient data from such event triggered sensors may be collected along with other patient data.

In block 404, the wearable medical device detects a subject medical event being experienced by a patient. Various patient data including data, such as ECG's, from various sensors are assessed to determine a medical event is occurring for the patient. At times a combination of patient data is used to make the determination of a medical event. Examples of detecting medical events via a wearable device is described in U.S. Publication No. 2023/0071214, "Multi-Function Wearable Monitoring System With Sleep Disorder Warning", filed on Sep. 2, 2022, the contents of which is incorporated herein by reference.

In some implementations, in response to the detection of the medical event, a wearable medical device enabled with a treatment unit provides treatment of the medical event to the patient. Treatment by the wearable device may include various degrees of care. Treatment may include life-sustaining actions by the wearable device, actions that maintain patient health until further help arrives, actions that address one aspect of the medical event but not all needs of the patient, actions that make the patient comfortable, etc. Along with the treatment provided by the wearable medical device, additional care is typically required to be administered by a trained support person. At times, treatment provided by the wearable device may continue during intervention by the trained support person where the wearable device is maintained intact on the patient.

Some medical support systems may not include any treatment of the patient. For example, some wearable medical devices are configured for only monitoring patient parameters and not provide treatment. Other wearable devices may generally provide treatment for other medical events and are not configured to treat the current medical event.

In block 406, in response to detecting the medical event, the wearable device initiates steps to establish wireless communication with a communication device of a support person within a short-range communication location of the patient. Such initiation steps can include transmitting via a short-range communication mechanism, e.g., broadcasting, an alert that a local patient is experiencing or has experienced a medical event. The initial alert information may include basic information about the medical event, such as a type of medical event, e.g., SCA and/or a degree of urgency for medical care, e.g., red for a time critical emergency and yellow for a medical event that is less time sensitive. General location of the patient may also be provided in the initial alert. The degree of urgency may be assessed by the wearable device by analysis of the patient data indicating the medical event. The receipt of the alert provides a notification that situation information is available to be transmitted upon acceptance of the connection by the communication device.

The wearable device waits for a response from a nearby communication device. When the wearable device receives a connection request response from the communication device approving the connection to access to situation information, the wearable device may be paired with the communication device. In some cases, more than one communication device may accept the connection, in which case the support system may establish more than one short-range connection with more than one communication devices. In some implementations in which more than one response is received, the support system may select a communication device to connect with using various selection criteria, such a support person who is closest in proximity to the patient, a level of expertise of the support person, the first response received by the wearable device, etc. A communication device may be notified by the wearable device if another support person is available to assist the patient and the wearable device may provide the trained support person an opportunity to decline attending to the patient in lieu of the other support person lending care.

In block 408, certain patient data is processed that relate to the medical event. Patient data may include general information about patient attributes to assist the trained support person in spotting the patient. The patient description information may be particularly useful when the patient is in a crowded setting. The patient data may include particular patient location information such as GPS coordinates, address, business name of the site of the patient, map showing a route to direct the trained support person to the patient, etc.

In some implementations, one or more situation factors may be employed to select patient data needed for the situation report. In some implementations, the situation factors may also include support resource availability. For example, the support system may prompt the trained support person to input responses to availability questions, such as availability of tools/equipment that can help in the care, number of trained support persons available on the scene, etc. In this manner, the situation report may be adapted to the resources at the disposal of the trained support person. The medical support system may use natural language processing to discern the answers of the trained support person.

Situation factors can also include an event time period for medical event-related patient data. The event time period may depend, at least in part, on the nature of the medical event. For example, for a sudden cardiac event, a shortened time period immediately prior to the detection of the medical event may be pertinent, e.g., 15 minutes prior to detection of the medical event. For a medical event that characteristically builds over time, such as a diabetes emergency, the event time period may be extended, such as hours before the medical event. The situation factors may include one or more patient attributes, characteristics of the medical event, and/or one or more characteristics of the wearable medical device.

Processing of patient data includes forming of situation information, such as extracting certain patient data, putting the data into context with other data, and/or formatting. In some implementations, patient data is selected for processing based on satisfying situation factors, such as a relevant time period. Some patient data used for situation reports may be time-independent data, e.g., prior medical history of the patient, known patient characteristics, such as disabilities, sensitivities, etc. The relevant situation information may include patient context during the event time period. For example, a prior patient activity level, a type of prior patient activity, a prior location of the patient, a patient current state or prior state, one or more vital signs of the patient, and combinations thereof.

In decision block 410 it is determined whether there is more situation information to be used in the situation report. For example, if there is additional patient data needed for the report during the time period, additional patient data is processed. If there is no further situation information, the situation information is formatted in block 412, otherwise, the process returns to block 408 to extract/process the additional situation information. It should be recognized that formatting may also be included in the processing step in block 408.

In block 412, formatting of the situation information may depend on the situation report, medical event, type of communication mechanism employed, and/or other considerations. In some implementations, situation information is formatted by inserting indications in the situation information to specify one or more fields of the situation report to be used for inclusion of the indicated situation information by the reporting application.

In some implementations, in order for a trained support person to gain access to an advanced (high) tier situation report, the trained support person may be required to satisfy an identification verification, such as enter a password into the medical support system, satisfy a biometric authentication (e.g., scanning of fingerprint, facial recognition, iris recognition, etc.), input answers to security questions, scanning a badge, card, or other article having a security object, etc. Such security inputs by the trained support person may be compared to stored data previously registered with the medical support system. In some implementations, once a trained support person has been authorized to access a particular tier of situation report, a reporting application is installed on a personal communication device. In some implementations the reporting application identifies a level of preauthorization for the trained support person and communicates the preauthorization to the wearable medical device and/or remote computing device of the medical support system. At times, preauthorization is for an organization that the trained support person belongs rather than the individual, such as a medical service group registered with the medical support system.

In some implementations, authentication of the trained support person may be made by authentication of the communication device of the trained support person. The communication device of the trained support person may be a personal device, such as a smartphone, smart watch, tablet, etc. Authentication may be made via a certificate of the reporting application, which may be activated by pairing of the communication device with the wearable device, such as via a rapid communication connection. In other situations, the communication device may be a dedicated device for a level of experience trained support person carried by the trained support person to pair with or otherwise communicate with the medical support system.

In block 414, the formatted situation information is transmitted to the communication device of the trained support person. Various communication connections may be used, such as an NFC tag scanned by the wearable device, infrared transmissions, BLE connections as described with regards to FIG. 4, and other short-range connections described in this description.

Figure 5:
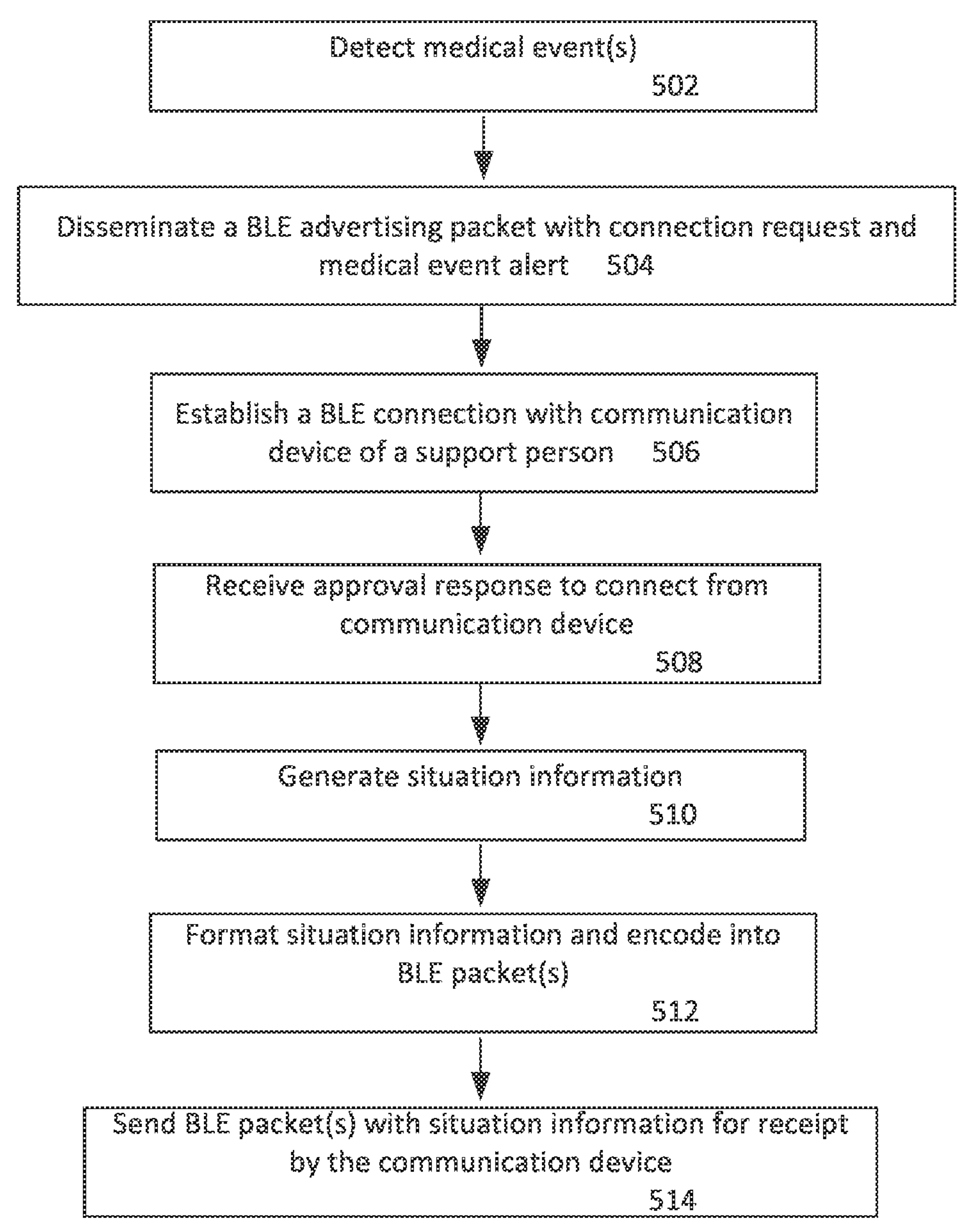
FIG. 5 is a flowchart of an example method for providing access to a situation report using a BLE communication connection, in accordance with some implementations.

FIG. 5 shows a flowchart of an example medical support process 500 for enabling access to situation reports through a BLE short-range connection. A trained support person uses the communication device to connect with the wearable device of the medical support system.

In block 502, one or more medical events experienced by a patient is recognized by the wearable medical device being worn by the patient. Such detection of medical events may include the processes described in FIG. 4, step 404 above and elsewhere in this description. At times, multiple related medical events are experienced by the patient within an event time period. Such multiple medical events may be detected by the wearable medical device and each individually or collectively serve to trigger a BLE advertising packet a described below.

As a result of detecting of the medical event(s), the wearable device attempts to locate and establish a short-range connection with a communication device of a nearby support person to assist the patient. In block 504 BLE advertising packet(s) is/are disseminated, such as broadcast advertising packets by a beacon of the wearable medical device, for receipt by one or more communication devices of trained support persons within a short-range receiving distance from the patient. The receiving distance depends on the BLE technology employed, such as 30 meters outdoors, and may be farther such as 100 meters outdoors. The receiving distance for BLE packet receipt is typically less than 50 meters, depending on any obstructions and interferences. However, advances in BLE technology may allow for farther receiving ranges to employ the medical support system.

The connectable advertising packet serves as a request for connection with the wearable device. The reporting application on the receiving end of the communication device may discovery the advertising packet and recognize the advertising packet as a notification that a patient is nearby experiencing a medical event and that situation report is available. The BLE advertising packet often has limited data carrying capacity and the bulk of the situation information may be encoded in subsequent data packets. For example, the advertising packet may have 31 bytes of available space for initial help data to be encoded. The help data should be sufficient for the receiving support person to decide on whether to help the patient or capability to help particular ailment. The help data may be encoded in a manner that is easy to translate on the receiving side to limit the amount of data space needed in the packet. For example, bit zero may generally mean a life threatening event is detected. The next couple of bits, such as next two bits, may indicate a type of ailment, such as heart related. In some implementations, a registered UUID for basic description of a medical event may be encoded as help data in the advertising packet. The reporting application may cross reference the decoded UUID to determine the type of medical event of the nearby patient.

The help data in the advertising packet may also include general locality of the patient. For example, the help data may include notification of a general geographic location, such as cardinal direction, of the patient. In some implementations, the help data may include information that can be used by the reporting application or other components of the communication device to determine geographic location. Such location information useable by the reporting application may include a media access control (MAC) address of the wearable device (e.g., via the advertising packet data or wearable device manufacturing data stored by the reporting application), internet protocol address, etc. In some implementations, the support system, e.g., the wearable device, may include a tracking element, such as a magnetic sensor or compass, a GPS device, etc. Location information may be used, for example, to triangulate the location of the wearable device. It may also be understood that the patient is within a certain receiving distance of the communication device to enable the short-range connection with the wearable device.

In some implementation, patient location may be determined by a GPS device of the wearable device or other computing device of the patient in communication with the wearable device. Such location tools may be activated in response to the wearable device detecting the medical event.

In block 506, upon receipt of a connection request response from the communication device approving the connection to access to situation information, a BLE connection is established by the wearable device as a one-to-one connection with the communication device of the trained support person. In some implementations, the BLE connection is made with the reporting application running on the communication device (for example running in the background while other applications are being used). The reporting application may monitor BLE traffic and when it finds a pattern that matches a predefined BLE pattern indicating a medical event alert, the reporting application may launch a browser or screen of the reporting application on the communication device displaying a user interface to connect and enable user input accepting the BLE data packets from the wearable medical device.

The reporting application may be dedicated software for the purpose of connecting with a particular wearable medical device for detecting certain types of medical events, such as cardiovascular events, other categories of wearable medical devices, or for the purpose of connecting with a wider variety of wearable medical devices. In some implementations, the communication device may be a medical treatment device that can be employed in treating the medical event, such as an AED, and the reporting application resides in software of the treatment device. In some implementations, the reporting application may be integrated with a general health and/or fitness application that runs on a multi-purpose communication devices, such as smart phones, tablets, smart watches, etc.

The receipt of the BLE advertising packet may trigger the application to display a user interface in which the trained support person may interface with the medical support system. In some implementations, receipt of the BLE advertising packet may trigger a pop up notification to appear on a display of the communication device. In still some implementations, receipt of the BLE advertising packet may trigger an audio alert, vibration, or other indication on the communication device.

In some implementations, receipt of the BLE advertising packet may enable the trained support person to interface with the medical support system through a browser of the communication device, rather than the reporting application. In block 508, a request for the situation report may be received by the medical support system. The request may be made in response to the trained support person interacting with a user interface of the reporting application, such as activating (e.g. clicking on) an interface element on the user interface, inputting a voice command, or other forms of input.

In some implementations, the trained support person may opt to reject receipt of the BLE advertising packet, data packets,/or and refuse further information regarding the medical event of the patient. For example, the trained support person may activate a reject interface element on the user interface or simply ignore the notification and not interface with the medical support system within a defined period of time, such as the critical time for care. For example, when a trained support person does not feel qualified to address the medical event or is unavailable to provide assistance, the trained support person may reject further interaction with the medical support system regarding the medical event. Furthermore, should the trained support person move outside of the receiving range for BLE transmissions, the trained support person may not receive further BLE packets and in some cases will cease to interact with the medical support system for the current medical event unless the trained support person connected with the remote computing device of the support system prior to traveling away from the patient.

In some implementations, the situation report application may enable the trained support person to forward the notification/alert of a nearby medical event to another trained support person to assist the patient. Once the alternative trained support person is within receiving range of the wearable device, the BLE communication connection may additionally be made with the communication device of this additional trained support person, as described above.

In block 510, the situation report may be generated as described above, for example as describe with regards to FIG. 4. In block 512, a BLE packet may be encoded with a UUID in the payload for a service to provide a situation report for a medical event. The BLE communication may include transmitting a persistent unique identifier (PUID) for the medical device.

The UUID may specify standard care instructions for the trained support person to refer to in caring for a medical event. In such implementations, the standard care instructions may be provided as preliminary information for initiating care in the BLE packet or otherwise transmitted, displayed, or output to the trained support person. The situation report may provide more comprehensive and patient-specific care information than such standard instructions. Examples of such preliminary care information may include, for ventricular fibrillation, standard instructions to find an AED. A finding of an asystole event may be associated with standard instructions to perform CPR. A detected fall experienced by a patient may result in standard instructions to look for wounds or assess for a seizure.

The situation report may provide more comprehensive situation information than the standard information indicated by the UUID, such as a fall that resulted from another detected medical event may be associated with instructions to treat the initiating medical event first. In some cases, the situation report may override the standard procedures for care specified by the UUID for the medical event. For example, the situation report may specify that a standard treatment is not advised due to particular characteristics of the patient, environmental conditions, history of the patient, or other reasons. In some implementations, an UUID may be specific for characteristics of the type of situation information provided to the trained support person. For example, the UUID may specify that situation information is provided for arrythmia treatment, such as ECG data.

In block 514, the BLE packets encoded with the situation information are sent from the wearable medical device. For example, a summary page of the situation report may be about 250 kilobytes that can take about 20-30 seconds to transmit to the communication device. The wearable device may send situation information for a previous predefined time period, such as such as an ECG data from the previous 10 seconds or patient data from the occurrence of the latest episode during the medical event. Depending on the situation information, multiple packets may be stacked or subpackets used for a greater volume of situation information. An example of a data packet may include about 182 bytes of available data that may be used for encoded situation information, in addition to header information. Extended packets may also be used for additional available data space. Stacked packets may be used, for example, to relay streaming situation information. The wearable device can send to the communication the number of packets being sent, such as 40 packets with situation information and the reporting application then knows to look for 40 packets.

The data packets are unpacked by the reporting application and translated into a situation report. Situation information may need to be further processed, such as converted into other formats, e.g., visual representations (such as plots) on a graph. For example, an ECG in a situation report may be transmitted as situation information including x-y coordinate data, e.g., voltage levels over time, that are translated by the reporting application as graphical representations plotted on a graph for display. In some implementations, the reporting application may use a specified minimum resolution for the x axis and minimum resolution for the y axis as a basis to interpret the situation information received to put together the ECG. Such access to the situation report is described below, for example with regards to FIG. 5.

In some implementations, the BLE data packets may also include patient spotting information in the payload to assist the trained support person in locating the patient. The patient spotting information may include a physical description of the patient, e.g., height, hair color, race, gender, weight, etc., and/or location information that pinpoints the specific or general site of the patient. Such location information may include GPS coordinates information, a description of the objects around the patient, address, business name of the location, distance between the trained support person and the patient, map directions to the patient, etc.

In some implementations, the communication connection may be bidirectional and the communication device can initiate requests for information to the medical support system. For example, the trained support person can send to the wearable device, a BLE packet encoded with a request for particular information in a situation report, such as an ECG. The request for information may be driven by the reporting application and the situation information needed for a particular situation report for the medical event. The request may also be in response to user input requesting the information, which may include requests for additional information after initial situation information is provided. Other ways of transmitting a request from the communication device to the wearable medical device and/or remote computing device are possible.

In response to a request for information, the requested situation information may be transmitted to the communication device. For example, the situation report may be dynamically viewed and updated as needed on the fly to enable viewing of some (additional) situation information and/or to restrict viewing of certain situation information. In some cases, such as when high tier details, such as patient sensitive information is requested by the trained support person, the trained support person may need to be checked as being pre-authorized prior to providing the requested information. For example, the medical support system may confirm that the situation reporting application on the communication device indicates pre-authorization of the trained support person.

Other communication connections between the wearable medical device and a communication device of the trained support person are possible. For example, the wearable medical device may include an infrared port to transmit infrared signals to the communication device, similar to a BLE packet described above. The communication device may be enabled for infrared communications with an infrared receiver and/or transmitter, e.g., according to Infrared Data Association (irDA) specifications, such as a smartphone or specialized medical treatment device, e.g., AED. The irDA port of the communication device may be held to the wearable device in a position free of objects blocking the communication path. The wearable device may provide written instructions, such as on a display or text on a label, for the trained support person on steps to connect via infrared communication, such as activating the irDA port of the communication device.

In some implementations, the trained support person may have a near field communication (NFC) enabled device that includes a unique NFC tag readable by an NFC reader of the wearable medical device. In some implementations, the wearable medical device may be triggered to scan for the NFC tag upon detection that the patient experiences a medical event requiring intervention by the trained support person. At other times, the NFC scanning mechanism may remain dormant. In this manner, battery life of the wearable medical device may be preserved for times in which a trained support person is needed. For example, the trained support person may have pre-installed the NFC tag consistent with the certain level of expertise onto the communication device. In other implementations, the trained support person may have another dedicated item that includes the NFC tag, such as a wristband, card, badge, key fob, token, etc.

Figure 6:
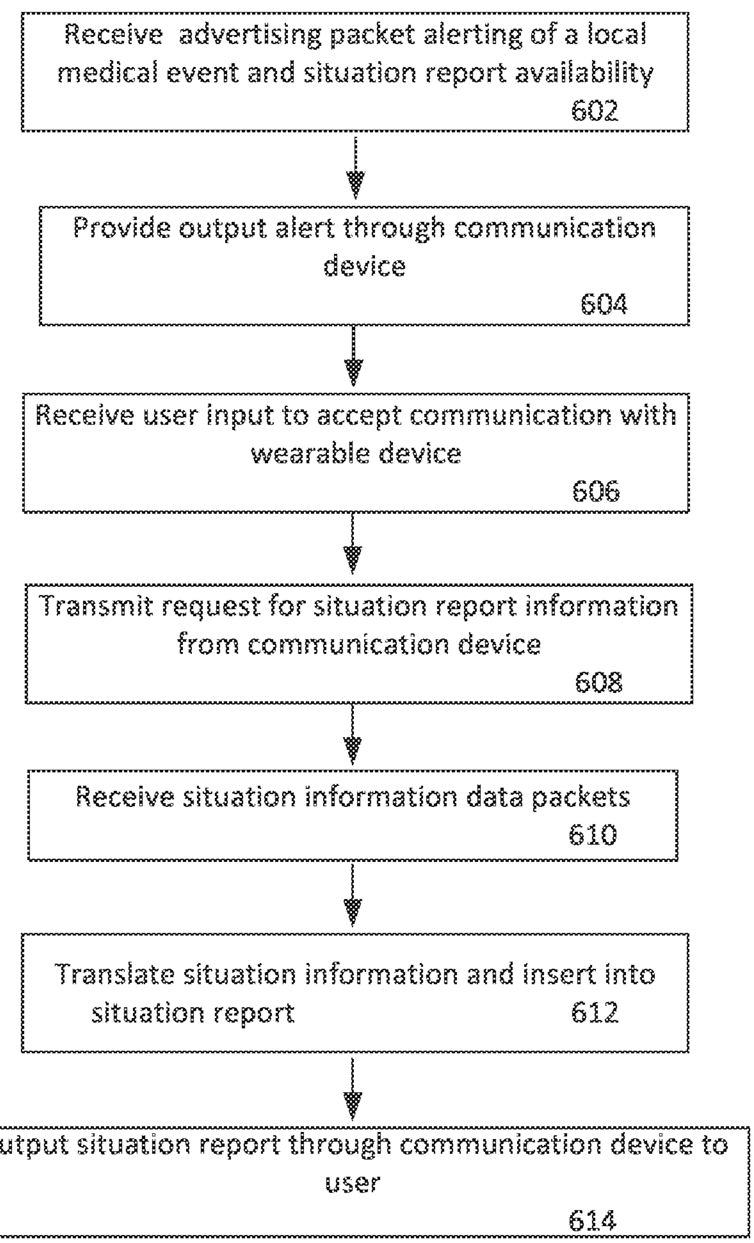
FIG. 6 is a flowchart of an example method for a reporting application to generate situation reports using received situation information, in accordance with some implementations.

FIG. 6 is a flow chart showing an example method for a communication device of a trained support person to generate situation reports using situation information received from the wearable device. All of some of the steps shown in FIG. 6 may be performed by a reporting application running on the communication device. Often, the reporting application is pre-installed on the communication device prior to receiving an alert of a medical event and invitation to connect with the wearable device. In other implementations, the reporting application may be installed on the fly when a patient experiencing a medical event is discovered. In such cases, installation of the reporting application may be sent by the wearable device to the communication device, e.g., via BLUETOOTH, WiFi Direct, APK file transfer, etc. The reporting application may also be installed on the spot by an appropriate online application store. In still some implementations, the reporting application may be a software component of another base application to provide a communication feature with the wearable device. The base application may be various types of applications, such as a software application commonly used on a smartphone or other device for multiple purposes, where the reporting application may be built on a platform that is readily available and universally used. The base application may also be specifically geared toward healthcare providers and encompass other features used by emergency care providers.

In block 602, the communication device receives an alert that serves as notification to the trained support person that a local patient experiencing a medical event and as a connection request for the trained support person to access a situation report via the communication device. The alert is received via a short-range communication, such as broadcast advertising packets from the wearable device. As such, only communication devices within a short-range communication distance from the wearable device receives the alert. The alert is further described above with regard to FIG. 4, block 406 and FIG. 5, block 504.

The communication device may include an observer (as in 250 of FIG. 2) that scans for medical related transmissions. Upon receiving the alert of the medical event from the wearable device, the communication device may, for example in response to user input, either launch the reporting application or install the reporting application. The launched application may then receive situation information and process the situation report as described in the block steps below.

In block 604, the alert information is output through the communication device to inform the trained support person. For example, a display of the communication device may show alert information, such as a location of the patient, type of medical event, degree urgency required to care for the patient, physical attributes of the patient, etc. The location of the patient may be indicated by distance from the communication device (e.g., a number of feet), a description of the location, such as at ABC store and address, GPS coordinates, etc. The alert may also include audio notification, such as a designated alert tone.

In block 606, the reporting application may receive user input to accept or reject the request for connection to access the situation report for the subject patient. A user interface may be displayed on a display screen of the communication device with a prompt for the user to submit an acceptance or rejection of the connection request. For example, the user may activate a display element (e.g., touch a button) to select acceptance or rejection.

In block 608, in response to user input accepting the connection, the reporting application may send back to the wearable device a request response approving the connection to access the situation report. An I/O interface, such as 210 in FIG. 2, may be employed to receive user input (in block 606) and/or send a response to the wearable device (in block 608).

In block 610, the reporting application receives data packets from the wearable device that are encoded with situation information formatted for the reporting application to be able to translate. In some implementations, the data packets may include services data packets with a main command structure and characteristics data packets with an address, software version, protocol of the software to communicate the message In block 612, the reporting application translates the situation information and inserts the information into a template or form of the situation report, thus generating a situation report for the subject medical event of the patient. For example, the reporting application decodes the incoming packets and unpacks the situation information. The reporting application recognizes areas of the situation report to insert the situation information. In some cases, the situation information is processed by the reporting application to integrate the situation information in a readable manner in the situation report. For example, the reporting application may recognize certain values in the situation information as data points on a graph, e.g. ECG, and the reporting application processes the data points to complete the graph on a display according to the read values. Other processing is possible to create clear situation reports that are easy to read, based on the situation information.

In block 614, the generated situation report is output through the communication device, such as visually displayed on a display of the communication device. At times, the situation information may include a stream of situation information that is used to update the situation report upon receipt of the steaming data packets. For example, current ECG data may be received, integrated with the situation report on the fly and displayed to the trained support person. There may be data processing lag, such as a few seconds behind in receiving situation information from currently collected patient data.

Some or all of the medical support processes 400 in FIG. 4, 500 in FIG. 5, and 600 in FIG. 6, or any other processes described herein, or variations and/or combinations of those processes, may be performed under the control of one or more computer systems configured with executable instructions and/or other data, and may be implemented as executable instructions executing collectively on one or more processors. For example, the medical support process 400, 500 and/or 600 may be adapted to include steps for treating a patient, such as a defibrillator shock based on the determined episodes.

Figure 7:
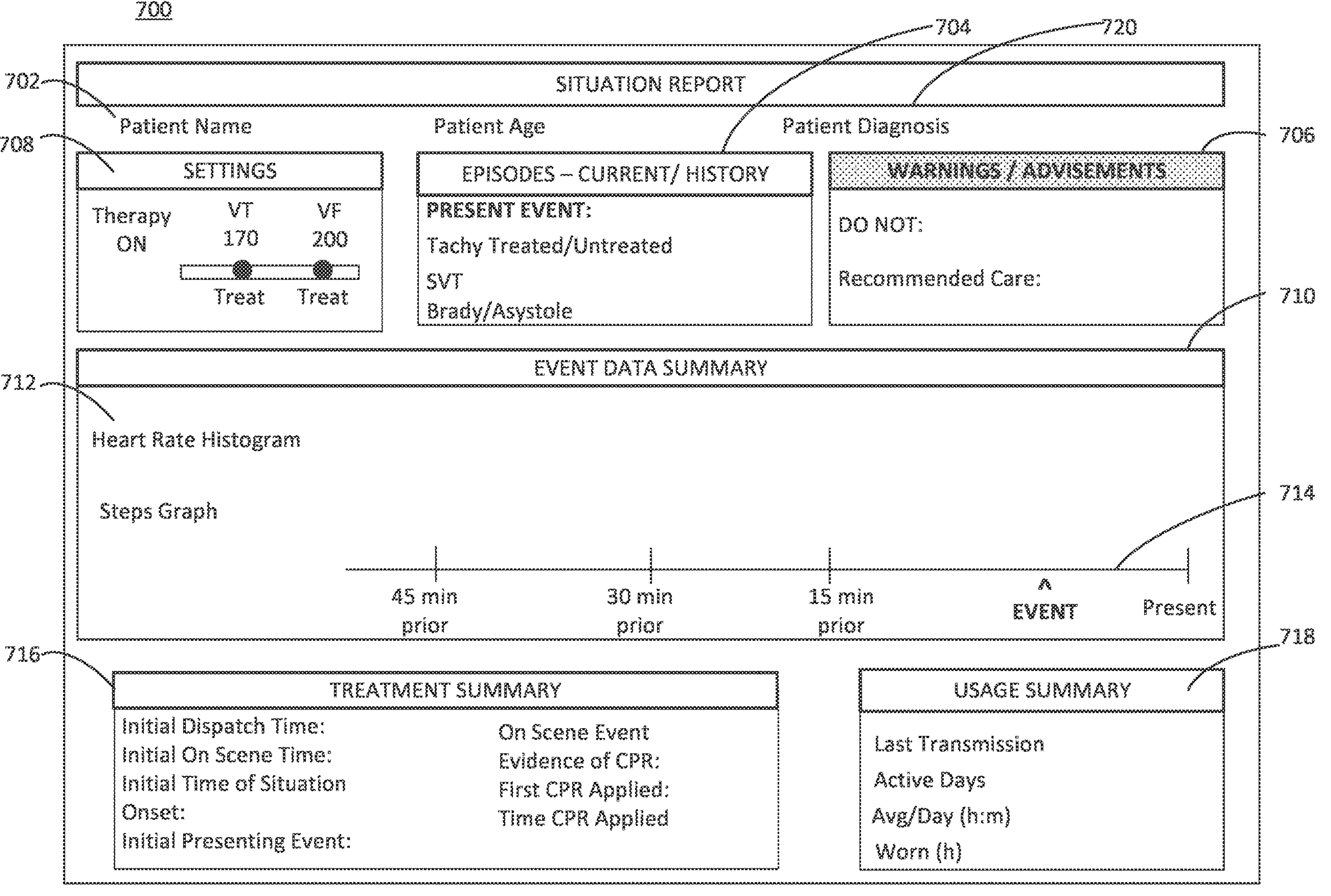
FIG. 7 is an example of a situation report including situation information, in accordance with some implementations.

FIG. 7 shows an example situation report 700 for displaying various situation information integrated into the situation report. The situation report may be based on a situation report template that may be specific for a particular medical event type or a general template may be adapted to be used for a particular medical event type. The situation report template includes one or more fields for inclusion of the situation information. For simplification purposes, the situation report 700 shown in FIG. 7 is illustrated with fields (described below) for inclusion of the situation information and example situation information is not shown. It should be understood that the situation report includes situation information, such as ECG's inserted into the appropriate fields. For example, portions of the situation information may be formatted with indications that specify which of the fields correspond with portions of the situation information to be inserted by the reporting application. Indications may include field labels (titles) and subfield labels.

The example situation report 700 includes fields for patient identifying information 702, such as patent name, patient age (or date of birth, year of birth, and the like). In some implementations, visual identifier information may also be provided to provide the support person with physical characteristics of the patient. The situation report may further include a diagnoses field 720 for previous and/or present diagnosis information of the patient. The diagnoses situation information may pertain to the current medical event, the purpose of the wearable device, or other relevant diagnoses that may assist a trained support person in providing care to the patient.

An episodes section 704 may provide for fields for situation information on the type of the current detected medical event. Past history of medical events and treatments by the wearable device may also be inserted into the episodes section 704.

In some implementations, a warnings/advisements section 706 may include a field that warns the support person to avoid implementing certain care/treatment for the patient. Recommended care tips and/or instructions may be also provided to assist the trained support person in providing care. For example, based on a history or characteristics of the patient, certain care may be advised that may not necessarily be otherwise known to the support person.

A settings section 708 may be provided to with information on certain settings of the wearable device. In the example shown, a treatment setting is on. Predesignated treatment parameters include a treatment for VT at 170 and a treatment for VF at 200.

An event data summary section 710 may include fields 712 devoted to sensor derived situation information from the wearable device, such as heart rate histogram information (ECG), steps graph to show activity of the patient, etc. Other types of data may include respiration, etc. The data may be provided against a timeline 714 that may include an appropriate time period before the medical event, a marker for the time of the medical event, and/or post medical event data. Trend information that summarizes data for one or more parameters may be also provided.

A present treatment summary section 716 may provide a quick look up of relevant data regarding treatment, such as an initial dispatch time as to when the support person is notified of the medical event (e.g., support person communication device may communicate confirmation), time the support person arrives on the scene (e.g., support person provides on-site verification such as pressing an "on-scene" button on the wearable device), and initial time of the medical event onset, an initial presenting event, medical events that occur while the support person is on the scene (e.g., progress of the medical event from VT to VF), evidence of CPR (e.g., as identified by the wearable device), when CPR is first applied (e.g., since the time of the onset of the medical event), time of CPR (e.g. from the first CPR applied to removal of the wearable device), etc.

In some implementation of situation report, a section may be provided on usage of the wearable device summary 718. For example, a time of a last report being transmitted, e.g., transmission to a server, days the wearable device has been active on the patient, average hours per day that the wearable device is active and hours worn.

Figure 8:
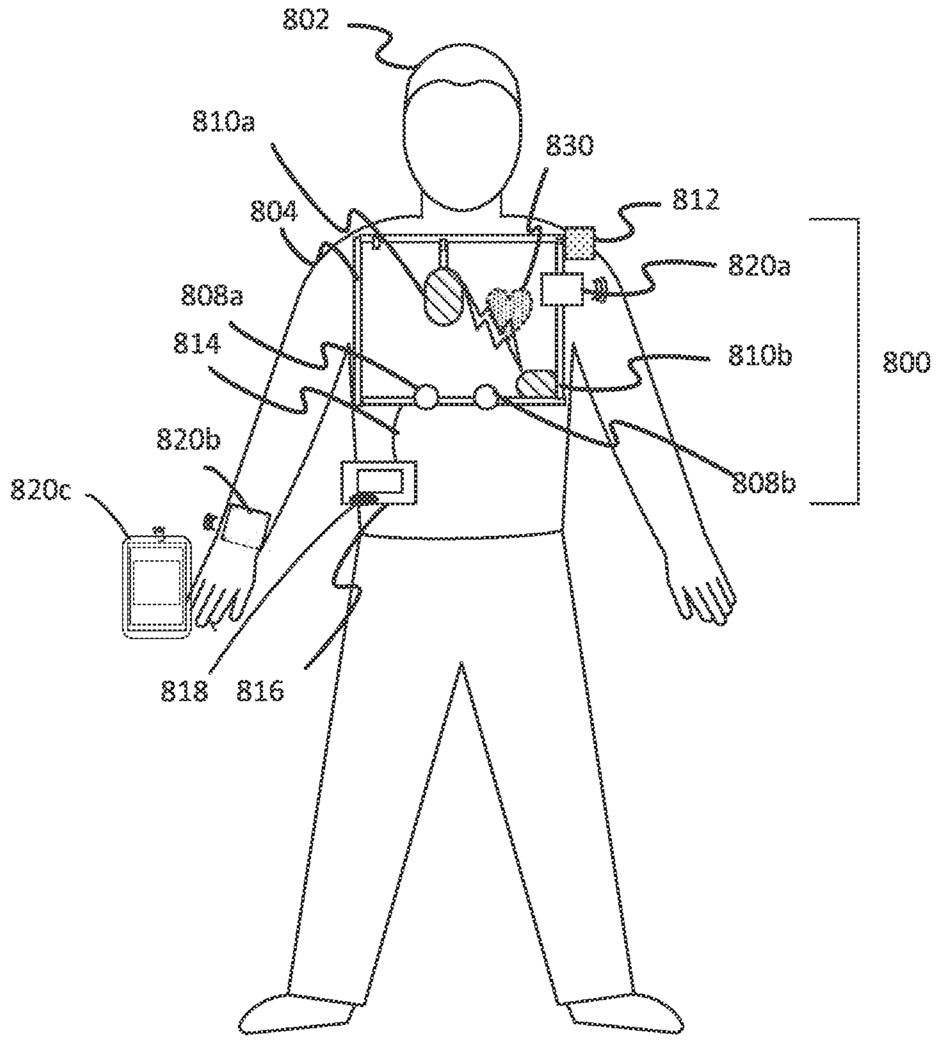
FIG. 8 is a schematic diagram of a wearable medical device including a vest-type wearable article with components, including a treatment unit, for use in the medical support system, in accordance with some implementations.

FIG. 8 shows an example of a wearable medical device incorporating a treatment unit in the form of a wearable cardioverter defibrillator (WCD) 800 configured with components for cardiac monitoring and treatment. Other treatment units are possible with other types of wearable medical devices to treat patients experiencing various medical events.

The situation report 700 is provided for illustration purposes of one example. Other formats, fields, arrangement of sections and fields, types of situation information, are possible. The situation report may cover less than a page, a page of information, or more than a page.

The WCD 800 includes a vest-type wearable article 804 that houses various components such as electrode sensors, one or more sensor 812, and an electronic main unit 816 in communication with the components of the wearable article 804. In some implementations, the main unit 816 may be carried by the patient separately from the wearable article 804, such as with a purse, belt, strap over the shoulder, and so on.

The main unit may include an interface port 818 to perform various short-range communication connections, such as broadcasting a BLE advertising packet and BLE data packets encoded with the situation information, sending RFID signals with the situation information embedded, transmitting the situation information with NFC, sending Zigbee signals for the situation information, and emitting a pattern of audio signals corresponding to the situation information.

The main electronic unit 816 may encase various software components of the wearable device 800. For example, the main unit 816 may include the data collection module 204 and/or situation information processing module 206 with reference to FIG. 2, and/or various subcomponents.

In some implementations, the wearable article 804 is configured for continuous wear (e.g., for at least several hours per day, and for at least several days, even a few months) by a patient 802, as may be prescribed by a medical provider. The wearable article 804 (also referred to as a "support structure") may be worn under clothing and has multiple ECG electrodes 808*a*, 808*b* that contact the skin of the patient at particular locations on the patient torso in order to monitor the cardiovascular condition of the patient when in use. Defibrillation electrodes 810*a*, 810*b* are positioned when in use to contact the skin of the patient at torso locations to discharge electrical charge. More than two ECG electrodes can be used and distributed around a patient's body.

Some aspects of the WCD 800 include a housing and an energy storage module (not shown) within the housing. The energy storage module can be configured to store an electrical charge. Other components can cause at least some of the stored electrical charge to be discharged via electrodes 810*a*, 810*b* through the patient, so as to deliver one or more defibrillation shocks through the patient. A lubricant may also be ejected from one or more ports (not shown) in the wearable device 800 near or at the electrodes for conductive contact.

The main electronic unit 816 may initiate defibrillating treatment using defibrillation electrodes 810*a*, 810*b*, or hold-off defibrillation, based on a variety of inputs, and/or signal outputs, including the ECG signal obtained using ECG electrodes 808*a*, 808*b*.

The plurality of electrodes 808*a*, 808*b*, 810*a*, 810*b*, can be coupled to a processor and/or main unit 816 via one or more cables 814, such as a therapy cable and/or ECG leads. ECG electrodes 808*a*, 808*b* and/or defibrillation electrodes 810*a*, 810*b* can be configured to be worn by a patient 802 in a number of ways. For instance, electrodes 808*a*, 808*b*, 810*a*, 810*b* can be coupled to the wearable article 806, directly or indirectly. The wearable article 806 can be configured to be worn by patient 802 so as to maintain electrodes on the body of the patient, often while the patient is moving around, etc. The electrodes can be thus maintained on the body by being attached to the skin of patient, or by being pressed against the skin directly or through garments, etc. In some embodiments the electrode is not necessarily pressed against the skin, but becomes biased that way upon sensing a condition that could merit intervention by the WCD system.

Using electrodes 808*a*, 808*b* the WCD can detect a shockable rhythm and administer a brief, strong electric pulse (e.g., shock, defibrillation shock, therapy, electrotherapy, therapy shock) through the body of the patient through defibrillation electrodes 810*a*, 810*b* in attempts to bring back a normal heart rhythm. The electric pulse is intended to go through and restart the heart 830, in an effort to save the life of patient 802. In some instances, the electric pulse can include one or more pacing pulses of lesser magnitude to simply pace the heart 830 if needed.

The wearable device 800, according to some implementations, can obtain various additional patient data from patient 802. To gather such patient data, the medical device may optionally include one or more sensor(s) 812 (including electrodes 808*a*, 808*b*, 810*a*, 810*b*). In some implementations, the sensor 812 could be provided as a standalone device, for example separate from the wearable article 804 or housing of the WCD 800. Sensor 812 may include one or more sensor in an array or a plurality of independent sensors, may be physically coupled to, in communication with, or integrated with the wearable article 804 or other medical device components. Such communication can be implemented by a communication module, as will be deemed applicable by a person skilled in the art in view of this description.

Sensor 812 can be configured to sense or monitor at least one local parameter, such as a parameter of patient 802, a parameter of the WCD system, and/or a parameter of the environment. The sensor 812 renders a signal responsive to the sensed parameter. The signal may be interpreted as quantitative data, such as values of a sensed parameter, or qualitative data, such as a comparison of the data to a threshold value. In some implementations, the signal is in qualitative form, such as informing whether or not a threshold is met, and so on. Sometimes these inputs about patient 802 are also referred to herein as physiological inputs and patient inputs. In embodiments, a sensor can be construed more broadly, as encompassing many individual sensors.

The sensors may include the electrodes described above. Other examples of sensors may include a perfusion sensor, a pulse oximeter, a device for detecting blood flow (e.g. a Doppler device), a sensor for detecting blood pressure (e.g. a cuff), an optical sensor, illumination detectors and sensors working together with light sources for detecting color change in tissue, a device that can detect heart wall movement, a sound sensor, a device with a microphone, a Saturation of Peripheral Oxygen (SpO2) sensor, a GPS, patient temperature thermometer, pressure sensors, optical sensors such as photoplethysmography, etc. to produce signals used in generating health data about the patient. An audio detector, e.g., microphone, such as heart-sound/phonocardiogram may be positioned to detect frequency, volume, intensity, regularity, etc. of internal body functions, such as heartbeat. The microphone may also detect frequency, volume, regularity, etc. of breaths.

Various patient communication devices 820*a*, 820*b*, 820*c* may be employed for interaction with the trained support person, remote computing device, the patient, etc. Interactions may include output of situation information, input a level of expertise of a trained support person, output instruction information, input authentication information, scan a bar code to access particular information, etc. Various types of patient communication devices may include an interface port, shown by example as 818 on main unit 816. Examples of patient communication devices may include a microphone/speaker component 820*a* of the wearable article 804, a smartwatch 820*b* of the patient, a mobile phone 820*c*, and the main unit 816. In some implementations the microphone/speaker component 820*a* may output a pattern of audio signals corresponding to the situation information, for a rapid communication connection. Other patient communication devices are possible that employ various input and/or output modalities. The patient communication device may also be located on a wearable article component of the medical device and can include a touch screen, a speaker, etc.

The wearable article 804 can be implemented in many different ways. For example, it can be implemented in a single component or a combination of multiple components. In embodiments, the wearable article 804 could include a vest, a half-vest, a garment, etc. In such embodiments such items can be worn similarly to analogous articles of clothing. In embodiments, the wearable article 804 could include a harness, one or more belts or straps, etc. In such embodiments, such items can be worn by the patient around the torso, hips, over the shoulder, etc. In embodiments, wearable article 804 can include a container or housing, which can even be waterproof. In such embodiments, the support structure can be worn by being attached to the patient's body by adhesive material, for example as shown and described in U.S. Pat. No. 8,024,037. The wearable article 806 can even be implemented as described for the support structure of US Pat. App. No. US2017/0056682, which is incorporated herein by reference. Of course, in such embodiments, the person skilled in the art will recognize that additional components of the WCD system can be in the housing of a support structure instead of being attached externally to the support structure, for example as described in US Pat. App. No. US2017/0056682.

There can be other examples as well. It will be understood that the wearable article 806 is shown only generically in FIG. 8, and in fact partly conceptually. FIG. 8 is provided merely to illustrate concepts about wearable article 804 and is not to be construed as limiting how the wearable article 804 is implemented, or how it is worn. The wearable article 804 shown in FIG. 8 illustrate a vest-type garment wearable medical monitoring device. In some implementations, the medical monitoring device may take various forms or combination of forms. For example, the wearable structure may include one or more patches, one or more bands, and/or a torso fitted garment to house various components of the medical monitoring device.

Figure 9:
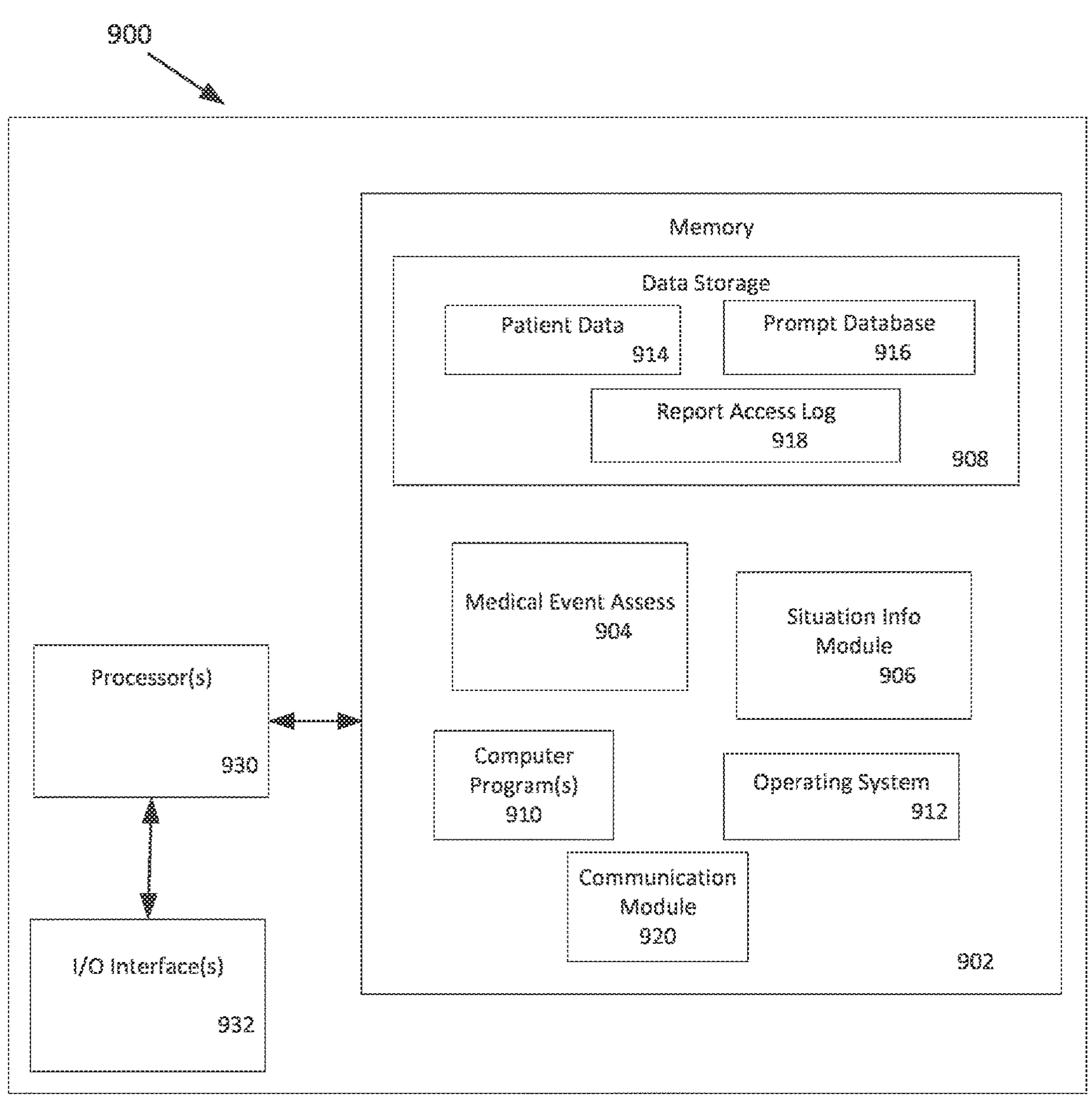
FIG. 9 is a block diagram illustrating an example functional components of the wearable medical device upon which at least some of the medical support processes may be implemented, in accordance with some implementations.

FIG. 9 shows an example wearable medical 900, such as 202 in FIG. 2, which may implement some of the medical support processes described herein. The wearable medical device 900 may include memory 902, processor 930, and I/O interface 932. The various elements of the wearable medical device 900 are shown in FIG. 9 as discrete/separate elements for purposes of illustration and explanation. According to some implementations, it is possible to combine some of these elements into a single element or device, while in other implementations of the medical support system, these elements may be distributed across a network such as in a cloud computing network. For example, functions of the medical support system may be performed by one or both of the multiple wearable medical device in a distributed network to provide information to other various devices of the support system and/or third party devices and perform other tasks as a service. Some of the components and functions depicted in wearable medical device 900 may be provided by the remote computing device (item 214 in FIG. 2) in addition to or instead of wearable medical device 900.

The processor 930 processes instruction for execution within the wearable medical device 900 including instructions stored in memory 902 or on the data store 908. The processor 930 may coordinate computing device components, e.g. applications, wireless or wired communication through interfaces, etc. In some implementations, multiple processors and buses may be used.

In some implementations, processor 930 may include intelligent hardware, e.g., a central processing unit (CPU), a microcontroller, an application specific integrated circuit (ASIC), etc. The processor 930 may be implemented in a number of ways. Such ways include, by way of example and not limitation, digital and/or analog processors such as microprocessors and Digital Signal Processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

The processor 930 may be implemented as a chipset of chips that include separate and multiple analog digital processors. The processor may also be implemented using various architectures. For example, the processor 930 may be a CISC (Complex Instruction Set Computer) processor, RISC (Reduced Instruction Set Computer) processor or MISC (Minimal Instruction Set Computer) processor, mobile device processors, etc.

The "processor" as used herein, includes any suitable hardware and/or software system, mechanism or component that processes data, signals, or other information. A processor may include a system with a general-purpose central processing unit, multiple processing units, dedicated circuitry for achieving functionality, or other systems. Processing need not be limited to a geographic location, or have temporal limitations. For example, a processor may perform its functions in "real-time," "offline," in a "batch mode," etc. Portions of processing may be performed at different times and at different locations, by different (or the same) processing systems.

Processor 930 may include, or have access to, a non-transitory storage medium, such as a memory 902, which can work together with processor 930. The memory 902 is for storing information within the remote computing device 900. Memory 902 may include various dynamic storage devices, coupled to a bus for storing information and instructions to be executed by the processor 930. The memory 902 may also be used for storing temporary variables or other intermediate information during execution of instructions to be executed by the processor 930. Such instructions, when stored in non-transitory storage media accessible to the processor 930, render the remote computer system 900 into a special-purpose machine that is customized to perform the operations specified in the instructions.

Memory 902 can include programs for processor 930, which processor 930 may be able to read and execute. More particularly, the programs can include sets of instructions in the form of code, which processor 930 may be able to execute upon reading. Executing is performed by physical manipulations of physical quantities, and may result in functions, operations, processes, actions and/or methods to be performed, and/or the processor to cause other devices or components or blocks to perform such functions, operations, processes, actions and/or methods. The programs can be operational for the inherent needs of processor 930, and can also include protocols and ways that decisions can be made.

The memory 902 may be any suitable data storage, memory and/or non-transitory computer-readable storage media, including electronic storage devices such as random-access memory (RAM), read-only memory (ROM), magnetic storage device (hard disk drive or the like), flash, optical storage device (CD, DVD, or the like), magnetic or optical disk, or other tangible media suitable for storing instructions (e.g., program or software instructions) for execution by the processor 930. For example, a tangible medium such as a hardware storage device can be used to store the control logic, which can include executable instructions. The instructions can also be contained in, and provided as, an electronic signal.

Data store 908 may store various data including patient data 914 that may be gathered (e.g., generated and/or collected) by the wearable device or other data input sources and/or generated by the wearable medical device 900.

Data store 908 may further include a prompt database 916 that stores prompts (such as standard instructions to care for a medical event) to be used for a trained support person for a particular medical event. For example, the prompt database 616 may include one or more tables organizing various prompts, such as instructions on care, instructions on how to access the situation report, request for input of trained support person information such as a level of expertise, warnings, basic background information about the wearable device and/or medical event, etc. The tables may associate such prompts with different medical events. When a medical event is identified, the prompts may be included in the situation report or presented automatically prior to receiving the situation report.

Data store 908 may further include a report access log 918 that stores descriptions of times that a situation report and situation information was previously or currently accessed such as previous and current situation reports and/or situation information (such as a reference to the stored situation report/situation information), medical event associated with the situation report/situation information, time of access, level of expertise of the trained support person, identification and/or contact information for the trained support person, location of trained support person when accessing the situation report/situation information, mode of communicating the situation information, etc.

In some implementations, at least a portion of information may be stored on a disk drive or other computer readable storage device (not shown) within the remote computing device 900. Such storage device include a floppy disk device, a hard disk device, an optical disk device, or a tape device, digital cards, a flash memory or other similar solid state memory device, or an array of devices.

Memory 902 further includes a situation information processing module 906 of the memory 902, as described above with regards to FIG. 2. The situation information processing module 906 may employ various processing and formatting methods described above, such as regarding 408-412 in FIGS. 4 and/or 510-512 in FIG. 5, and Various modules or other computer programs 910, also referred to as programs, software, software applications or code, are stored within memory 902 and contain instructions that, when executed, perform one or more methods, such as those described herein. In some implementations, and as a matter of convention used herein, instances of the software may be referred to as a "module" and by other similar terms. Generally, a module includes a set of the instructions so as to offer or fulfill a particular functionality. Implementations of modules and the functionality delivered are not limited by the implementations described in this document. The computer program may be tangibly embodied in an information carrier such as computer or machine readable medium, for example, the memory 902, storage device or memory on processor 930. A machine readable medium is any computer program product, apparatus or device used to provide machine instructions or data to a programmable processor.

Any suitable programming languages and programming techniques may be used to implement the routines of particular embodiments. Different programming techniques may be employed such as procedural or object-oriented. The routines may execute on a single processing device or multiple processors. Although the steps, operations, or computations may be presented in a specific order, the order may be changed in different particular embodiments. In some particular embodiments, multiple steps shown as sequential in this specification may be performed at the same time.

A number of implementations have been described. Features described with conditional language may describe implementations that are optional. The functional blocks, methods, devices, and systems described in the present disclosure may be integrated or divided into different combinations of systems, devices, and functional blocks as would be known to those skilled in the art.

The wearable medical device 900 may implement the techniques described herein using customized hard-wired logic, one or more ASICs or FPGAs, firmware and/or program logic which in combination with the computer system causes or programs the device 900 to be wearable medical a special-purpose machine. According to one implementation, the techniques herein are performed by the wearable medical device 900 in response to the processor 930 executing one or more sequences of one or more instructions contained in the memory 902. Such instructions may be read into the memory 902 from another storage medium. Execution of the sequences of instructions contained in the memory 902 causes the processor 930 to perform the process steps described herein.

In alternative implementations, one or more methods can be implemented in hardware (logic gates, etc.), or in a combination of hardware and software. Example hardware can be programmable processors (e.g. Field-Programmable Gate Array (FPGA), Complex Programmable Logic Device), general purpose processors, graphics processing units (GPUs), Application Specific Integrated Circuits (ASICs), and the like. One or more methods can be performed as part of or component of an application running on the system, or as an application or software running in conjunction with other applications and operating system 912.

The wearable medical device 900 further includes the operating system 912. Any operating system 912, e.g., server OS, that is supports the medical support processes described herein performed by the wearable medical device 900 may be employed.

The communication module 920 may perform tasks for short-range communications with a support communication device via Input/Output (I/O) interface 932. The communication module 920 may also include software that enables communications of a user interface over a network such as the HTTPS, TCP/IP, RTP/RTSP, protocols, wireless application protocol (WAP), IEEE 802.11 protocols, and the like. In addition to and/or alternatively, other communications software and transfer protocols may also be used, for example IPX, UDP or the like. The communication network may include a local area network, a wide area network, a wireless network, an Intranet, the Internet, a private network, a public network, a switched network, or any other suitable communication network, such as for example cloud networks. The network may include many interconnected computer systems and any suitable communication links such as hardwire links, optical links, satellite, or other wireless communications links such as BLE, Infrared, NFC, Zigbee, BLUETOOTH, Wi-Fi, wave propagation links, or any other suitable mechanisms for communication of information. For example, the network may communicate to one or more mobile wireless devices, such as mobile phones, tablets, and the like, via a wireless transceiver.

The Input/Output (I/O) interface 932 can interface to other input and output devices. In some implementations, the I/O interface 932 can connect to interface devices such as input devices (keyboard, pointing device, touchscreen, microphone, camera, scanner, sensors, etc.) and/or output devices (display devices, speaker devices, printers, motors, etc.). Some implementations can provide a microphone for capturing sound (e.g., as a part of captured images, voice commands, etc.), audio speaker devices for outputting sound, or other input and output devices.

The devices and/or systems described in this document perform functions, processes and/or methods. These functions, processes and/or methods may be implemented by one or more devices that include logic circuitry. Such a device can be alternately called a computer, and so on. It may be a standalone device or computer, such as a general purpose computer, or part of a device that has one or more additional functions. The logic circuitry may include a processor and non-transitory computer-readable storage media, such as memories, of the type described elsewhere in this document. Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described above. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, and so on.

This detailed description includes flowcharts, display images, algorithms, and symbolic representations of program operations that may be provided within at least one non-transitory, tangible, computer readable medium for execution by the one or more processors. Flowcharts as in FIGS. 4, 5, and 6 are used to describe both programs and also methods. So, while flowcharts described methods in terms of blocks, they also concurrently describe programs. It is also within the spirit and scope to implement a program or code that can be stored in a machine-readable medium, such as logic including software instructions encoded in one or more non-transitory media for execution by the one or more processors, to permit a computer to perform any of the methods described above.

Other embodiments include combinations and sub-combinations of features described or shown in the drawings herein, including for example, embodiments that are equivalent to: providing or applying a feature in a different order than in a described embodiment, extracting an individual feature from one embodiment and inserting such feature into another embodiment; removing one or more features from an embodiment; or both removing one or more features from an embodiment and adding one or more features extracted from one or more other embodiments, while providing the advantages of the features incorporated in such combinations and sub-combinations. As used in this paragraph, feature or features can refer to the structures and/or functions of an apparatus, article of manufacture or system, and/or the steps, acts, or modalities of a method.

What is claimed is:

1. A method for a cardioverter defibrillator support system to provide local access to a situation report for assisting a patient, the method comprising:

gathering patient data by a wearable cardiac device (WCD) worn by a patient;

determining by the WCD, that the patient experiences a medical event including one or more arrythmias when the patient is at a location away from a medical treatment site, based at least in part, on the patient data;

initiating defibrillation treatment for the one or more arrythmias by the WCD;

processing at least a portion of the patient data to produce situation information associated with the medical event, wherein the processing includes formatting the situation information for inclusion in the situation report;

broadcasting, by the WCD, a connectable advertising packet that includes data about the medical event for a trained support person to use to decide to assist the patient and to accept a connection with the WCD to receive the situation information;

receiving an acceptance from a communication device of the trained support person;

in response to receiving the acceptance, establishing by the WCD, a short-range connection with the communication device of the trained support person; and transferring by the WCD, the situation information to the communication device via the short-range connection to generate the situation report at the communication device for use by the trained support person to administer treatment to the patient according to the situation information.

2. The method of claim 1, wherein establishing the short-range connection includes sending an invitation to the communication device to trigger launching of a reporting application on the communication device, and wherein the situation report is generated by the reporting application using the situation information.

3. The method of claim 2, wherein formatting the situation information includes inserting indications in the situation information to specify one or more fields of the situation report for inclusion of the situation information by the reporting application.

4. The method of claim 1, wherein transferring the situation information includes providing at least one of: an electrocardiogram (ECG) stream of the patient data of a current patient state recently captured by the WCD or one or more ECG snippets of a prior patient state previously captured patient data, and wherein the situation information includes patient data related to the defibrillation treatment.

5. The method of claim 1, wherein the short-range connection includes a BLUETOOTH Low Energy (BLE) connection, and wherein the method further comprises providing via the BLE connection, a first universally unique identification (UUID) for the medical event associated with arrythmia to specify a service that includes receiving situation information and a second UUID for characteristics of the situation information for arrythmia treatment.

6. The method of claim 1, further comprising:

providing patient spotting information including at least one of: patient location information or a physical description of the patient to assist in locating the patient.

7. The method of claim 1, further comprising:

providing to the communication device, a user prompt for the trained support person to enter the acceptance prior to the trained support person making physical contact with the patient at the location.

8. A method for a cardioverter defibrillator support system to provide local access to a situation report for assisting a patient, the method comprising:

determining, by a wearable cardiac device (WCD), that a patient experiences a medical event including one or more arrythmias when the patient is away from a medical treatment site, based at least in part, on patient data gathered by the WCD;

initiating defibrillation treatment for the one or more arrythmias by the WCD;

processing at least a portion of the patient data to produce situation information associated with the medical event; and in response to determining the medical event, establishing a Bluetooth Low Energy (BLE) connection with a communication device of a trained support person, wherein establishing the connection includes:

disseminating a BLE advertising packet for receipt by the communication device to advertise the medical event that includes data about the medical event for the trained support person to use to decide to assist the patient and to accept a connection with the WCD to receive the situation information for use by the trained support person to administer medical care to the patient;

receiving an acceptance for the connection from the communication device to access to situation information;

in response to receiving the acceptance, establishing a one-to-one connection with the communication device; and transferring by the WCD in a BLE data packet via the one-to-one connection, the situation information formatted for inclusion in the situation report generated by a reporting application running on the communication device.

9. The method of claim 8, wherein the BLE advertising packet includes sending an invitation to the communication device to trigger launching of the reporting application on the communication device.

10. The method of claim 8, wherein the BLE advertising packet and/or the BLE data packet includes patient spotting information including at least one of: patient location information or a physical description of the patient to assist in locating the patient.

11. The method of claim 8, wherein the BLE connection is bidirectional and the method further comprises:

receiving from the communication device, a request for particular additional situation information; and transferring by the WCD in one or more additional BLE packets, the additional situation information.

12. The method of claim 8, further comprising providing via the BLE connection, a first universally unique identification (UUID) for the medical event associated with arrythmia to specify a service that includes receiving situation information and a second UUID for characteristics of the situation information for arrythmia treatment.

13. The method of claim 8, wherein formatting the situation information includes inserting indications in the situation information to specify one or more fields of the situation report to be used for inclusion of the situation information by the reporting application.

14. The method of claim 8, wherein the situation information includes x and y coordinate data for the reporting application to create an electrocardiogram (ECG) for display on the communication device.

15. A cardioverter defibrillator support system to provide local access to a situation report for assisting a patient, the cardioverter defibrillator support system comprising:

a wearable cardiac device (WCD) that is wearable by the patient, the WCD comprising:

one or more sensors to collect patient data associated with the patient;

a patient assessment module to determine that the patient experiences a medical event including one or more arrythmias, based at least in part on the patient data;

a treatment unit to provide defibrillation treatment for the one or more arrythmias;

an interface to establish a short-range connection with a communication device of a trained support person in response to determining the medical event; and one or more processors and logic encoded in one or more non-transitory media for execution by the one or more processors and when executed operable to perform steps comprising:

processing, by a situation information module, at least a portion of the patient data to produce situation information associated with the medical event experienced by the patient when the patient is away from a medical treatment site, wherein the processing includes formatting the situation information for inclusion in the situation report;

broadcasting, by the WCD, a connectable advertising packet that includes data about the medical event for the trained support person to use to decide to assist the patient and to accept a connection with the WCD to receive the situation information;

receiving an acceptance from the communication device of the trained support person; and in response to receiving the acceptance, transferring the situation information to the communication device via the short-range connection during a critical time for care to generate the situation report for use by the trained support person to administer medical care to the patient according to the situation information.

16. The cardioverter defibrillator support system of claim 15, further comprising a reporting application for use by the communication device, configured to generate the situation report incorporating the situation information received from the WCD.

17. The cardioverter defibrillator support system of claim 16, wherein formatting the situation information includes inserting indications in the situation information to specify one or more fields of the situation report to be used for inclusion of the situation information by the reporting application.

18. The cardioverter defibrillator support system of claim 16, wherein the situation information includes x and y coordinate data and wherein the reporting application is further configured to translate the x and y coordinate data into graphic representations on an electrocardiogram (ECG) for display on the communication device.

19. The cardioverter defibrillator support system of claim 16, wherein the logic is operable to perform steps comprising:

transferring via the short-range connection, a first universally unique identification (UUID) for the medical event associated with arrythmia to specify a service that includes receiving situation information and a second UUID for characteristics of the situation information for arrythmia treatment.

20. The cardioverter defibrillator support system of claim 15, wherein the situation information includes information regarding previous treatment and/or immediate future treatment for the medical event.

* * * * *